(12) United States Patent
Colucci et al.

(10) Patent No.: US 8,637,671 B2
(45) Date of Patent: Jan. 28, 2014

(54) INDOLE DERIVATIVES AS CRTH2 RECEPTOR ANTAGONISTS

(75) Inventors: John Colucci, Kirkland (CA); Michael Boyd, Saint-Lazare (CA); Mohamed Helmi Zaghdane, Montreal (CA); Michel Gallant, Pierrefonds (CA)

(73) Assignee: Merck Canada Inc., Quebec (CA)

( * ) Notice: Subject to any disclaimer, the term of this patent is extended or adjusted under 35 U.S.C. 154(b) by 302 days.

(21) Appl. No.: 13/120,074

(22) PCT Filed: Sep. 17, 2009

(86) PCT No.: PCT/CA2009/001321
§ 371 (c)(1),
(2), (4) Date: Mar. 21, 2011

(87) PCT Pub. No.: WO2010/031183
PCT Pub. Date: Mar. 25, 2010

(65) Prior Publication Data
US 2011/0172263 A1    Jul. 14, 2011

Related U.S. Application Data

(60) Provisional application No. 61/192,787, filed on Sep. 22, 2008, provisional application No. 61/172,439, filed on Apr. 24, 2009.

(51) Int. Cl.
*C07D 471/04* (2006.01)
*A61K 31/437* (2006.01)

(52) U.S. Cl.
USPC ................................ 546/95; 546/94; 514/294

(58) Field of Classification Search
USPC ...................................... 546/94, 95; 514/294
See application file for complete search history.

(56) References Cited

U.S. PATENT DOCUMENTS

| | | |
|---|---|---|
| 7,618,979 B2 | 11/2009 | Leblanc et al. |
| 7,696,222 B2 | 4/2010 | Wang |
| 2008/0292626 A1 | 11/2008 | Wang et al. |
| 2010/0234415 A1 | 9/2010 | Berthelette et al. |
| 2011/0178115 A1 | 7/2011 | Leblanc et al. |
| 2011/0201641 A1 | 8/2011 | Wang |

FOREIGN PATENT DOCUMENTS

| | | |
|---|---|---|
| EP | 0384349 B1 | 2/1990 |
| WO | 2006125179 A1 | 11/2006 |
| WO | 2007/019675 A1 | 2/2007 |
| WO | 2009049021 A1 | 4/2009 |
| WO | 2010031182 A1 | 3/2010 |
| WO | 2010031184 A1 | 3/2010 |

OTHER PUBLICATIONS

Patani et al, 1996, Biosterism : A rational approach in drug design.*
Bit, R. A., et al., "Inhibitors of Protein Kinase C. 3. Potent and Highly Selective Bisindolylmaleimides by Conformational Restriction," Journal of Medicinal Chemistry, 1993, vol. 36, pp. 21-29.
Written Opinion issued by the International Searching Authority in connection with PCT International Application No. PCT/CA2009/001321, filed Sep. 17, 2009.
Notice of Allowance mailed Oct. 16, 2012 from U.S. Appl. No. 12/708,924, which application published as US2010/0234415.
Notice of Allowance mailed May 28, 2013 from U.S. Appl. No. 13/120,067, which application published as US2011/0178115.
European Communication pursuant to Article 94(3) EPC issued Aug. 27, 2013, corresponding to EP Application No. 09 813 945.4.

* cited by examiner

*Primary Examiner* — Rita Desai
(74) *Attorney, Agent, or Firm* — Eric A. Meade; Valerie J. Camara

(57) ABSTRACT

Compound of formula I are antagonists of the PGD2 receptor, CRTH2, and as such are useful in the treatment and/or prevention of CRTH2-mediated diseases such as asthma.

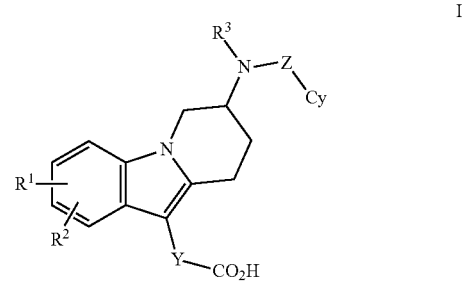

10 Claims, No Drawings

INDOLE DERIVATIVES AS CRTH2 RECEPTOR ANTAGONISTS

BACKGROUND OF THE INVENTION

Prostanglandin D2 ($PGD_2$) is a cyclooxygenase metabolite of arachidonic acid. It is released from mast and TH2 cells in response to an immunological challenge, and has been implicated in playing a role in different physiological events such as sleep and allergic responses.

Receptors for $PGD_2$ include the "DP" receptor, the chemoattractant receptor-homologous molecule expressed on TH2 cells ("CRTH2"), and the "FP" receptor. These receptors are G-protein coupled receptors activated by $PGD_2$. The CRTH2 receptor and its expression on different cells including human T-helper cells, basophils, and eosinophils are described in Abe, et al., *Gene* 227:71-77, 1999, Nagata, et al., *FEBS Letters* 459:195-199, 1999, and Nagata, et al., *The Journal of Immunology* 162:1278-1286, 1999, describe CRTH2 receptor. Hirai, et al., *J. Exp. Med.* 193:255-261, 2001, indicates that CRTH2 is a receptor for $PGD_2$.

WO2007019675 discloses CRTH2 antagonists of the formula:

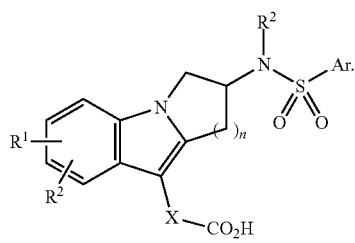

SUMMARY OF THE INVENTION

The present invention provides novel compounds which are CRTH2 receptor antagonists. Compounds of the present invention are useful for the treatment of various prostaglandin-mediated diseases and disorders; accordingly the present invention provides a method for the treatment of prostaglandin-mediated diseases using the novel compounds described herein, as well as pharmaceutical compositions containing them.

DETAILED DESCRIPTION OF THE INVENTION

The present invention relates to compounds of formula I:

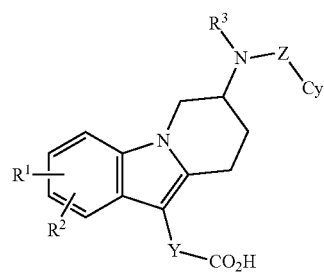

and pharmaceutically acceptable salts thereof, wherein:

Y is selected from —$C(R^a)(R^b)$—, —$C(R^a)(R^b)$—$C(R^a)(R^b)$—, —$C(R^a)$═$C(R^b)$—, —$OCH_2$—, —$OCH(C_{1-3}$alkyl)-, —$OC(C_{1-3}$alkyl$)_2$-, —$OC(CH_2)_{2-5}$—, —$SCH_2$—, —$SCH(C_{1-3}$alkyl)-, —$SC(C_{1-3}$alkyl$)_2$- and —$SC(CH_2)_{2-5}$—;

Z is —$C(O)$—$(C(R^d)(R^e))_n$— or —$C(O)$—$C(R^f)(R^g)$—$O$—, wherein n is 0, 1 or 2;

Cy is aryl, heteroaryl or $C_{3-6}$ cycloalkyl optionally fused to a benzene, each of which is optionally substituted with 1 to 4 groups independently selected from $R^e$;

$R^1$ is selected from H, halogen, —$OC_{1-6}$alkyl, and —$C_{1-6}$alkyl;

$R^2$ is selected from H, halogen, —$C_{1-6}$alkyl, —$OC_{1-6}$alkyl, —$SC_{1-6}$alkyl, —$S(O)C_{1-6}$alkyl, —$S(O)_2C_{1-6}$alkyl, —CN, aryl and heteroaryl;

$R^3$ is selected from H, $C_{1-6}$alkyl and benzyl optionally substituted on the phenyl portion with 1 to 3 halogen;

$R^a$ and $R^b$ are independently H, aryl, heteroaryl, $C_{1-6}$alkyl or halo$C_{1-6}$alkyl; or $R^a$ and $R^b$ together with the carbon atom to which they are both attached form a $C_{3-6}$cycloalkyl ring; or $R^a$ and $R^b$ together with the adjacent carbon atoms to which they are attached form a $C_{3-6}$cycloalkyl ring;

$R^c$ is selected from halogen, $NR^fR^g$, $SO_2NR^fR^g$, CN, $C_{1-6}$alkoxy, $C_{1-6}$alkyl, halo$C_{1-6}$alkoxy, and halo$C_{1-6}$alkyl;

$R^d$ and $R^e$ are independently selected from hydrogen, $C_{1-6}$alkyl, —$C_{1-6}$alkyl-$C_{3-6}$cycloalkyl, hydroxy, $C_{1-6}$alkoxy, $NR^fR^g$, and aryl optionally substituted with 1 to 3 groups independently; or $R^d$, $R^e$ together with the carbon atom to which they are both attached form a $C_{3-6}$cycloalkyl optionally having a ring heteroatom selected from —O—, —S—, —N(C(O)$R^f$)— and —N($R^f$)—, and optionally substituted with 1 to 3 $C_{1-3}$alkyl groups; or $R^d$, $R^e$ attached to adjacent carbon atoms together with the carbon atoms to which they are attached form a $C_{3-6}$cycloalkyl optionally having a ring heteroatom selected from —O—, —S—, —N(C(O)$R^f$)— and —N($R^f$)—, and optionally substituted with 1 to 3 $C_{1-3}$alkyl groups; and $R^f$ and $R^g$ are independently selected from hydrogen and $C_{1-3}$alkyl; or $R^f$, $R^g$ together with the atom to which they are both attached form a 3- to 6-membered ring.

In one subset of formula I are compounds wherein Cy is phenyl optionally substituted with 1 to 3 groups independently selected from $R^c$. In one embodiment thereof. Cy is phenyl optionally substituted with 1 to 2 groups independently selected from halogen, $C_{1-6}$alkyl, halo$C_{1-6}$alkyl and $C_{1-6}$alkoxy.

In another subset of formula I are compounds wherein Y is —$C(R^a)(R^b)$—. In one embodiment thereof Y is methylene.

In another subset of formula I are compounds wherein the chiral carbon to which the —$NR^3$—Z—Cy is attached has the (R)-configuration.

In another subset of formula I are compounds of formula Ia:

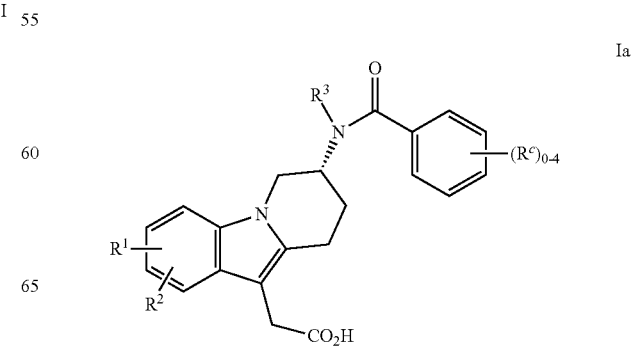

In another subset of formula I are compounds of formula Ib:

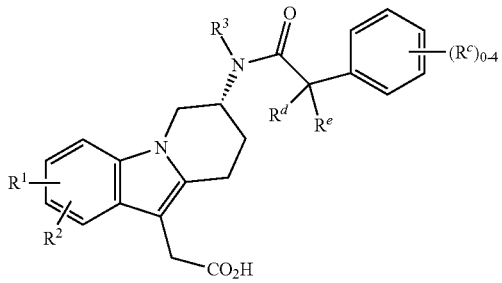

In one embodiment, at least one of $R^d$ and $R^e$ is other than hydrogen. In another embodiment $R^d$, $R^e$ and the carbon to which they are both attached together form a $C_{3-6}$-carbocycle optionally substituted with one or two $C_{1-3}$alkyl groups. In another embodiment $R^3$ is other than hydgrogen; in one group thereof $R^3$ is methyl.

The invention also encompasses pharmaceutical compositions containing a compound of formula I, and methods for treatment or prevention of prostaglandin mediated diseases using compounds of formula I.

The invention is described using the following definitions unless otherwise indicated.

The term "halogen" or "halo" includes F, Cl, Br, and I.

The term "alkyl" refers to linear or branched alkyl chains having the indicated number of carbon atoms. Non-limiting examples of alkyl groups include methyl, ethyl, propyl, isopropyl, butyl, s- and t-butyl, pentyl, hexyl, and the like.

"Haloalkyl" means an alkyl group as described above wherein one or more hydrogen atoms have been replaced by halogen atoms, with up to complete substitution of all hydrogen atoms with halo groups. $C_{1-6}$haloalkyl, for example, includes —$CF_3$, —$CF_2CF_3$, $CHFCH_3$, and the like.

"Alkoxy" means alkoxy groups of a linear or branched alkyl chain having the indicated number of carbon atoms. $C_{1-6}$alkoxy, for example, includes methoxy, ethoxy, propoxy, isopropoxy, and the like.

"Haloalkoxy" means an alkoxy group as described above in which one or more hydrogen atoms have been replaced by halogen atoms, with up to complete substitution of all hydrogen atoms with halo groups. $C_{1-6}$haloalkoxy, for example, includes —$OCF_3$, —$OCF_2CF_3$, —$OCH_2CF_3$ and the like.

"Aryl" means a 6-14 membered carbocyclic aromatic ring system comprising 1-3 benzene rings. If two or more aromatic rings are present, then the rings are fused together, so that adjacent rings share a common bond. Examples include phenyl and naphthyl.

The term "heteroaryl" (Het) as used herein represents a 5-10 membered aromatic ring system containing one ring or two fused rings, 1-4 heteroatoms, selected from O, S and N. Het includes, but is not limited to, furanyl, imidazolyl, isoxazolyl, isothiazolyl, oxadiazolyl, oxazolyl, pyrazolyl, pyridyl, pyrrolyl, tetrazolyl, thiazolyl, thiadiazolyl, thienyl, triazinyl, triazolyl, 1H-pyrrole-2,5-dionyl, 2-pyrone, 4-pyrone, pyrrolopyridine, furopyridine and thienopyridine.

"Therapeutically effective amount" means that amount of a drug or pharmaceutical agent that will elicit the biological or medical response of a tissue, a system, animal or human that is being sought by a researcher, veterinarian, medical doctor or other clinician.

The term "treatment" or "treating" includes alleviating, ameliorating, relieving or otherwise reducing the signs and symptoms associated with a disease or disorder.

The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of formula I, and pharmaceutically acceptable excipients.

The term "optionally substituted" means "unsubstituted or substituted," and therefore, the generic structural formulas described herein encompasses compounds containing the specified optional substituent as well as compounds that do not contain the optional substituent. For example, the phrase "aryl or heteroaryl each optionally substituted with 1 to 4 groups independently selected from $R^c$" encompasses unsubstituted aryl or heteroaryl, and aryl or heteroaryl substituted with one, two, three or four substituents selected from $R^c$; the same phrase can also be represented by the equivalent expression "Ar—$(R^c)_{0-4}$".

Each variable is independently defined each time it occurs within the generic structural formula definitions. For example, when there is more than one $R^e$ in "Ar—$(R^c)_{0-4}$" each $R^c$ is independently selected at each occurrence, and each $R^c$ can be the same or different from the other(s). In another example, the term —$OC(C_{1-3}alkyl)_2$- includes compounds in which the two alkyl substituents are of the same or different chain lengths. As a further example, for the term —$(C(R^d)(R^e))_n$—, when n is 2, each occurrence of $R^d$ and $R^e$ can be the same or different from the other occurrence of $R^d$ and $R^e$, respectively; for example, —$(C(R^d)(R^e))_2$— can be —$CH_2CH_2$—, —$CH(CH_3)CH_2$—, —$C(CH_2)_4$—$CH_2$—, and the like.

For purposes of this specification, the following abbreviations have the indicated meanings Ac=acetyl; ADD=azodicarboxylic acid dipiperidide; BOC=t-butoxycarbonyl; DCM=dichloromethane; DIPEA=diisopropylethylamine; DMAP=4-(dimethylamino)-pyridine; DMF=dimethylformamide; DMSO=dimethyl sulfoxide; HATU=O-(7-azabenzo-triazol-1-yl)-N,N,N',N'-tetramethyluronium hexafluorophosphate; MTBE=methyl t-butyl ether; NAD=β-nicotinamide adenine dinucleotide; PPTS=pyridinium p-toluene sulfonate; RT or rt=room temperature; TBAF=tetrabutylammonium fluoride; TBDMSi=t-butyldimethylsilyl; TEA=triethylamine; TFA=trifluoroacetic acid; THF=tetrahydrofuran; Alkyl group abbreviations include: Me=methyl; Et=ethyl; n-Pr=normal propyl; i-Pr=isopropyl; c-Pr=cyclopropyl; n-Bu=normal butyl; i-Bu=isobutyl; c-Bu=cyclobutyl; s-Bu=secondary butyl; t-Bu=tertiary butyl.

Optical Isomers—Diastereomers—Geometric Isomers—Tautomers

Compounds of formula I contain one or more asymmetric centers and can thus occur as racemates and racemic mixtures, single enantiomers, diastereomeric mixtures and individual diastereomers. The present invention is meant to comprehend all such isomeric forms of the compounds of formula I.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of formula I.

Compounds of the formula I may be separated into diastereoisomeric pairs of enantiomers by, for example, fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent.

Alternatively, any enantiomer of a compound of the general formula I may be obtained by stereo specific synthesis using optically pure starting materials or reagents of known configuration.

Salts

The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, unless otherwise specified, references to the compound of formula I, Ia, Ib, Ic and Id, subsets thereof, embodiments thereof, as well as specific compounds are meant to also include the pharmaceutically acceptable salts.

Furthermore, some of the crystalline forms for compounds of the present invention may exist as polymorphs and as such all forms are intended to be included in the present invention. In addition, some of the compounds of the instant invention may form solvates with water (hydrates) or common organic solvents. Such solvates are encompassed within the scope of this invention.

Utilities

The ability of compounds of formula I to interact with prostaglandin receptors makes them useful for preventing or reversing undesirable symptoms caused by prostaglandins in a mammalian, especially human subject. This mimicking or antagonism of the actions of prostaglandins indicates that the compounds and pharmaceutical compositions thereof are useful to treat, prevent, or ameliorate in mammals and especially in humans: respiratory conditions, allergic conditions, pain, inflammatory conditions, mucus secretion disorders, bone disorders, sleep disorders, fertility disorders, blood coagulation disorders, trouble of the vision as well as immune and autoimmune diseases. In addition, such a compound may inhibit cellular neoplastic transformations and metastic tumor growth and hence can be used in the treatment of cancer. Compounds of formula I may also be of use in the treatment and/or prevention prostaglandin-mediated proliferation disorders such as may occur in diabetic retinopathy and tumor angiogenesis. Compounds of formula I may also inhibit prostanoid-induced smooth muscle contraction by antagonizing contractile prostanoids or mimicking relaxing prostanoids and hence may be used in the treatment of dysmenorrhea, premature labor and eosinophil related disorders. More particularly compounds of formula I are antagonists of prostaglandin D2 receptor, CRTH2.

Accordingly, another aspect of the invention provides a method of treating or preventing a prostaglandin mediated disease comprising administering to a mammalian patient in need of such treatment a compound of formula I in an amount which is effective for treating or preventing said prostaglandin mediated disease. Prostaglandin mediated diseases include, but are not limited to, allergic rhinitis, nasal congestion, rhinorrhea, perennial rhinitis, nasal inflammation, asthma including allergic asthma, chronic obstructive pulmonary diseases and other forms of lung inflammation; sleep disorders and sleep-wake cycle disorders; prostanoid-induced smooth muscle contraction associated with dysmenorrhea and premature labor; eosinophil related disorders; thrombosis; glaucoma and vision disorders; occlusive vascular diseases; congestive heart failure; diseases or conditions requiring a treatment of anti-coagulation such as post-injury or post surgery treatment; inflammation; gangrene; Raynaud's disease; mucus secretion disorders including cytoprotection; pain and migraine; diseases requiring control of bone formation and resorption such as for example osteoporosis; shock; thermal regulation including fever; and immune disorders or conditions in which immunoregulation is desirable. More particularly the disease to be treated is one mediated by prostaglandin D2 such as nasal congestion, pulmonary congestion, and asthma including allergic asthma.

In one embodiment of the invention is a method of treating or preventing a prostaglandin mediated disease comprising administering to a mammalian patient in need of such treatment a compound of formula I in an amount which is effective for treating or preventing a prostaglandin mediated disease, wherein the prostaglandin mediated disease is nasal congestion, rhinitis including allergic and perennial rhinitis, and asthma including allergic asthma.

In another embodiment of the present invention is a method of treating or preventing a prostaglandin D2-mediated disease comprising administering to a mammalian patient in need of such treatment a compound of formula I in an amount which is effective for treating or preventing a prostaglandin D2 mediated disease wherein said prostaglandin D2 mediated disease is nasal congestion or asthma.

In another embodiment of the present invention is a method for the treatment of nasal congestion in a patient in need of such treatment which comprises administering to said patient a therapeutically effective amount of a compound of formula I.

In yet another embodiment of the present invention is a method for the treatment of asthma, including allergic asthma, in a patient in need of such treatment which comprises administering to said patient a therapeutically effective amount of a compound of formula I.

Dose Ranges

The magnitude of prophylactic or therapeutic dose of a compound of formula I will, of course, vary with the nature and the severity of the condition to be treated and with the particular compound of formula I and its route of administration. It will also vary according to a variety of factors including the age, weight, general health, sex, diet, time of administration, rate of excretion, drug combination and response of the individual patient. In general, the daily dose from about 0.001 mg to about 100 mg per kg body weight of a mammal, preferably 0.01 mg to about 10 mg per kg. On the other hand, it may be necessary to use dosages outside these limits in some cases.

The amount of active ingredient that may be combined with the carrier materials to produce a single dosage form will vary depending upon the host treated and the particular mode of administration. For example, a formulation intended for the oral administration of humans may contain from 0.05 mg to 5 g of active agent compounded with an appropriate and convenient amount of carrier material which may vary from about 5 to about 99.95 percent of the total composition. Dosage unit forms will generally contain between from about 0.1 mg to about 0.4 g of an active ingredient, typically 0.5 mg, 1 mg, 2 mg, 5 mg, 10 mg, 25 mg, 50 mg, 100 mg, 200 mg, or 400 mg.

Pharmaceutical Compositions

Another aspect of the present invention provides pharmaceutical compositions comprising a compound of formula I with a pharmaceutically acceptable carrier. For the treatment of any of the prostanoid mediated diseases compounds of formula I may be administered orally, by inhalation spray, topically, parenterally or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats, etc., the compound of the invention is effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water-miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of formula I may also be administered in the form of suppositories for rectal administration of the drug. These compositions can be prepared by mixing the drug with a suitable non-irritating excipient which is solid at ambient temperatures but liquid at the rectal temperature and will therefore melt in the rectum to release the drug. Such materials are cocoa butter and polyethylene glycols.

For topical use, creams, ointments, gels, solutions or suspensions, etc., containing the compound of formula I are employed. (For purposes of this application, topical application shall include mouth washes and gargles.) Topical formulations may generally be comprised of a pharmaceutical carrier, cosolvent, emulsifier, penetration enhancer, preservative system, and emollient.

Combinations with Other Drugs

For the treatment and prevention of prostaglandin mediated diseases, compound of formula I may be co-administered with other therapeutic agents. Thus in another aspect the present invention provides pharmaceutical compositions for treating prostaglandin mediated diseases comprising a therapeutically effective amount of a compound of formula I and one or more other therapeutic agents. Suitable therapeutic agents for combination therapy with a compound of formula I include: (1) a DP receptor antagonist such as S-5751; (2) a corticosteroid such as triamcinolone acetonide; (3) a β-agonist such as salmeterol, formoterol, terbutaline, metaproterenol, albuterol and the like; (4) a leukotriene modifier, including a leukotriene receptor antagonist such as montelukast, zafirlukast, pranlukast, or a lipooxygenase inhibitor including 5-lipooxygenase inhibitors and FLAP (5-lipooxygenase activating protein) inhibitors such as zileuton; (5) an antihistamine such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (6) a decongestant including phenylephrine, phenylpropanolamine, pseudophedrine, oxymetazoline, ephinephrine, naphazoline, xylometazoline, propylhexedrine, or levo-desoxyephedrine; (7) an antiitussive including codeine, hydrocodone, caramiphen, carbetapentane, or dextramethorphan; (8) another prostaglandin ligand including prostaglandin F agonist such as latanoprost; misoprostol, enprostil, rioprostil, ornoprostol or rosaprostol; (9) a diuretic; (10) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (11) cyclooxygenase-2 (COX-2) inhibitors such as celecoxib and rofecoxib; (12) inhibitors of phosphodiesterase type IV (PDE-IV) e.g. Ariflo, roflumilast; (13) antagonists of the chemokine receptors, especially CCR-1, CCR-2, and CCR-3; (14) cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (15) anti-diabetic agents such as insulin, sulfonylureas, biguanides (metformin), α-glucosidase inhibitors (acarbose) and glitazones (troglitazone, pioglitazone, englitazone, rosiglitazone and the like); (16) preparations of interferon beta (interferon beta-1a, interferon beta-1b); (17) anticholinergic agents such as muscarinic antagonists (ipratropium bromide and tiotropium bromide), as well as selective muscarinic M3 antagonists; (18) steroids such as beclomethasone, methylprednisolone, betamethasone, prednisone, dexamethasone, and hydrocortisone; (19) triptans commonly used for the treatment of migraine such as sumitriptan and rizatriptan; (20) alendronate and other treatments for osteoporosis; (21) other compounds such as 5-aminosalicylic acid and prodrugs thereof, antimetabolites such as azathioprine and 6-mercaptopurine, cytotoxic cancer chemotherapeutic agents, bradykinin (BK2) antagonists such as FK-3657, TP receptor antagonists such as seratrodast, neurokinin antagonists (NK1/NK2), VLA-4 antagonists such as those described in U.S. Pat. No. 5,510,332, WO97/03094, WO97/02289, WO96/40781, WO96/22966, WO96/20216, WO96/01644, WO96/06108, WO95/15973 and WO96/31206. In addition, the invention encompasses a method of treating prostaglandin $D_2$ mediated diseases comprising: administration to a patient in need of such treatment a nontoxic therapeutically effective amount of a compound of formula I, optionally co-administered with one or more of such ingredients as listed immediately above.

Methods of Synthesis

Compounds of Formula I of the present invention can be prepared according to the synthetic routes outlined in the following scheme(s) and by following the methods described herein.

In Scheme I, the amine 1 can be alkylated, for example with an alkyl iodide in the presence of a base such as NaH, to provide 2. Alternatively 1 can be subject to reductive amination conditions to give 2. Compounds I and 2 can be converted to the corresponding amide using HATU as coupling agent with an carboxylic acid or acylated with an acyl chloride, and the resulting product can be hydrolyzed to provide a compound of formula I using well known processes.

Scheme I

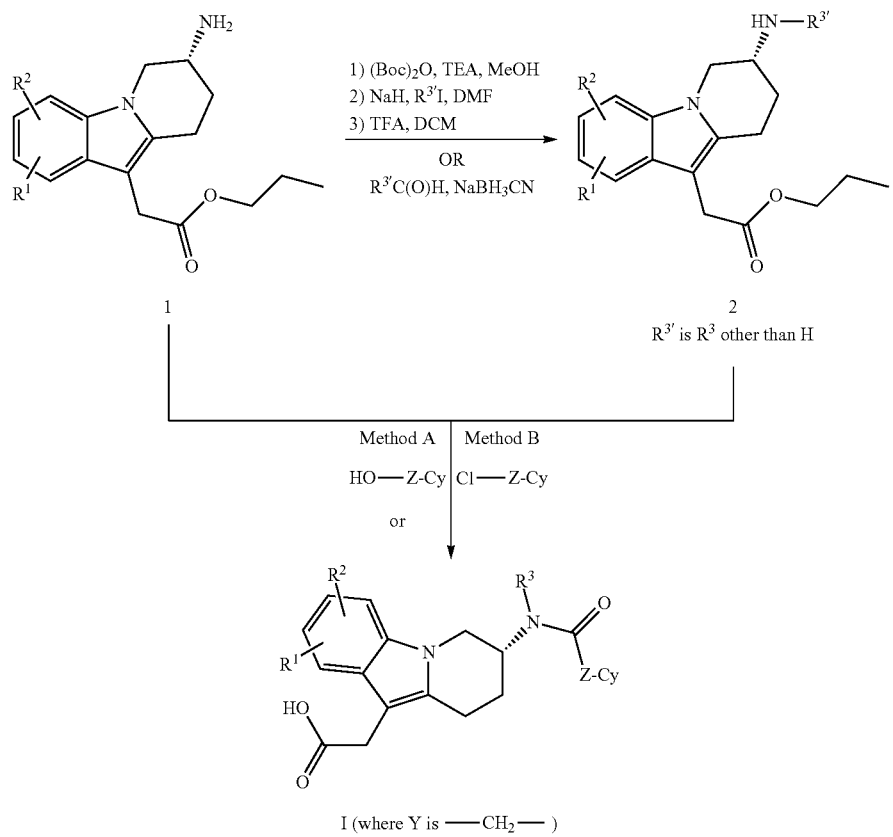

I (where Y is —CH₂— )

Compounds of formula I in which Y is other than methylene may be prepared according to the general procedures outlined in WO2007019675, the relevant portions are hereby incorporated by reference.

The following examples are provided to illustrate the invention only, and are not to be construed as limiting the scope thereof in any manner.

PREPARATION OF INTERMEDIATES

Propyl ([7R]-7-amino-6,7,8,9-tetrahydropyrido[1,2-a]indol-10-yl)acetate

Step 1: ethyl 3-(6-oxo-1-phenyl-1,4,5,6-tetrahydropyridazin-3-yl)propanoate

In a three neck flask equipped with a Dean-Stark trap, phenylhydrazine hydrochloride and diethyl 4-oxoheptanedioate (1 equiv.) were combined in toluene (1.15 M). The suspension was stirred 48 h at reflux. The reaction mixture was cooled to rt and concentrated under vacuum to afford the desired material as a brown oil which was used as such in the next step.

Step 2: propyl 3-[3-(2-oxo-2-propoxyethyl)-1H-indol-2-yl]propanoate

Methanesulfonic acid (1.15 equiv.) was added to a stirred solution of ethyl 3-(6-oxo-1-phenyl-1,4,5,6-tetrahydropyridazin-3-yl)propanoate from Step 1 in n-propanol (1.1 M). The mixture was stirred overnight at 80° C. The mixture was cooled to room temperature and neutralized with aqueous 1N NaOH (1 equiv.). Final mixture was concentrated under vacuum, diluted with toluene and concentrated again. The residue was purified by column chromatography on silica gel using automatized gradiant pump system CombiFlashRF (Teledyne ISCO) eluting with ethyl acetate/hexane (0:100 to 60:40) to give the title compound (79%) as a brown oil.

Step 3: 3-[3-(2-oxo-2-propoxyethyl)-1H-indol-2-yl]propanoic acid

Aqueous 8N KOH (1.05 equiv.) was added to a stirred solution of propyl 3-[3-(2-oxo-2-propoxyethyl)-1H-indol-2-yl]propanoate from Step 2 in n-propanol (0.5 M). The mixture was stirred at 50° C. for 4 h. The reaction mixture was cooled to rt, quenched with acetic acid (1.2 equiv.) and concentrated. The residue was purified on a pad of silica gel using $CH_2Cl_2$, then $CH_2Cl_2$/EtOAc (9/1) and finally $CH_2Cl_2$/EtOAc/MeOH (88/10/2) to afford after evaporation of the volatiles, the desired material (68%) as yellow oil.

Step 4: propyl [2-(4-diazo-3-oxobutyl)-1H-indol-3-yl]acetate

N-methylmorpholine (1.1 equiv.) was added dropwise over 1 h to a stirred, 0° C. mixture of 3-[3-(2-oxo-2-propoxyethyl)-1H-indol-2-yl]propanoic acid from Step 3 and ethyl chloroformate (1.11 equiv.) in THF (0.4 M). The reaction temperature was closely monitored during the addition and was not allowed to go over +2° C. The mixture was stirred at 0° C. an additional 30 min. A white precipitate formed rapidly. Diazomethane (0.3 M in $Et_2O$, 1.8 equiv.) was added and the final mixture was stirred for 2 h at 0° C. The mixture was filtered and the supernatant was concentrated under vacuum (with AcOH put in the vacuum trap to quench excess diazomethane). The residue was purified by column chromatography on silica gel using automatized gradiant pump system CombiFlashRF (Teledyne ISCO) eluting with EtOAc/Hexane(10:90 to 60:40) to give the title compound (63%) as a yellow solid.

Step 5: propyl (7-oxo-6,7,8,9-tetrahydropyrido[1,2-a]indol-10-yl)acetate

Rhodium (II) octanoate dimmer (0.1 equiv.) was added to a CH$_2$Cl$_2$ solution (0.02 M) of propyl [2-(4-diazo-3-oxobutyl)-1H-indol-3-yl]acetate from Step 4. The reaction mixture was stirred overnight at rt and then concentrated. The residue was purified by column chromatography on silica gel using automatized gradiant pump system CombiFlashRF (Teledyne ISCO) eluting with EtOAc/Hexane (2:98 to 10:90) to give the title compound (64%) as a yellow solid.

Step 6: propyl ([7R]-7-amino-6,7,8,9-tetrahydropyrido[1,2-a]indol-10-yl)acetate

Sodium phosphate, dibasic (3.8 equiv.) and sodium formate (266 equiv.) were added to a solution of D-alanine (38 equiv.) in water. The pH was measured as 7.6. NAD (0.04 equiv.), Pyridoxal-5-phosphate (0.11 equiv.), Lactate dehydrogenase (LDH) (1 equiv.), Formate dehydrogenase (FDH) (1 equiv.), and Amine-Transaminase ATA117 (1 equiv.) were added under stirring and slowly dissolved. The measured pH was 7.3. The mixture was aged at 22° C. for 1 h. The flask was flushed with nitrogen and propyl (7-oxo-6,7,8,9-tetrahydropyrido[1,2-a]-indol-10-yl)acetate from Step 5 was added as a DMSO (0.06 M) solution. The reaction was adjusted to pH 7.2 and aged at 30° C. overnight under nitrogen atmosphere. Upon completion of the reaction as determined by HPLC, the pH of the reaction was adjusted to pH 4.0 with 6N HCl and Celite (20 g per L) was added. After stirring for 1 hr the reaction was filtered through a Celite bed and the filter cake was washed twice with 0.1N HCl. The combined aqueous filtrate was extracted with 1 volume of MTBE. The organic layer did not contain amine and was discarded. The aqueous layer was diluted with an equal volume of MTBE and the pH of the mixture was adjusted to pH 9.5 using 5N NaOH. The two phases were separated and the aqueous layer was extracted with MTBE. The spent aqueous layer had no detectable amine and was discarded. The combined organic layers were washed with dilute sodium carbonate and dried over Na$_2$SO$_4$. Evaporation of the volatiles afforded the crude title compound (80%). The ee was determined as 99% by SFC assay.

Preparation of Intermediates

General Procedure

Compounds of types 1 and 2 can be prepared according to the procedure outlined in Schemes II and III. In Scheme II aspartic acid dimethyl ester II-i is treated with sulfonyl chloride II-ii in THF in the presence of triethylamine to afford the sulfonyl amide diester Reduction of the diester II-iii with e.g., sodium borohydride provides the diol II-iv, which, under Mitsunobu conditions, provides the aziridine II-v. The primary alcohol of II-v can be protected with a silyl ether group to give protected aziridine Scheme II

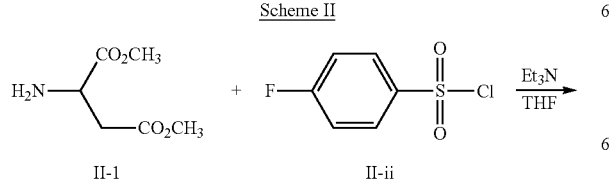

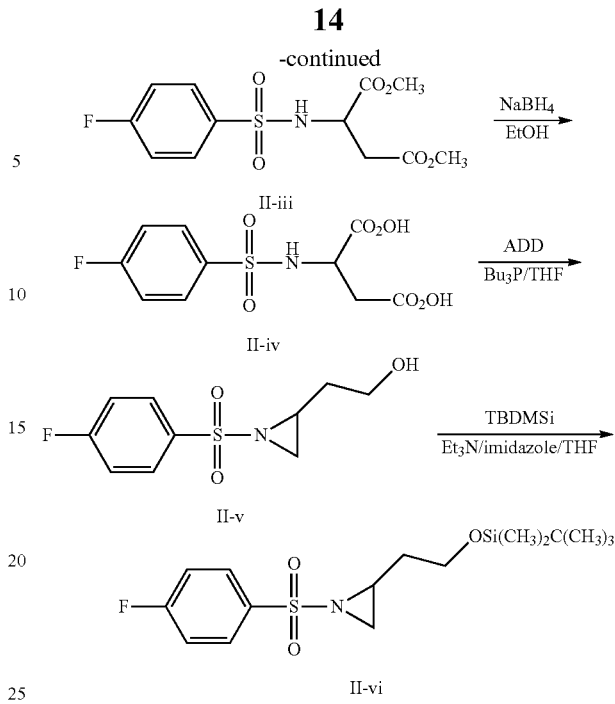

In Scheme III the indole III-i is condensed with the aziridine II-vi in the presence of sodium hydride to provide III-ii. The silyl group is removed with TBAF followed by oxidation with DMSO or a Dess-Martin reagent to afford the corresponding aldehyde which, when heated in toluene in the presence PPTS, provides the corresponding cyclized compound Hydrogenation of compound III-iv gives the sulfonamide III-v. Sulfonamide III-v, when treated with magnesium in methanol (See Monika Fitz Tetrahedron Asymmetry 2005, 16, 3690 for examples of sulfonamide cleavage), provides the amine III-vi.

Scheme III

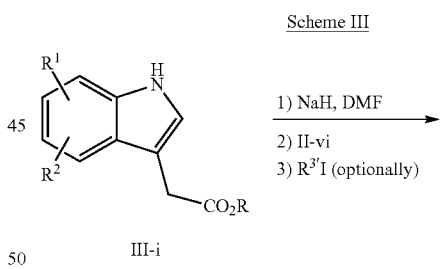

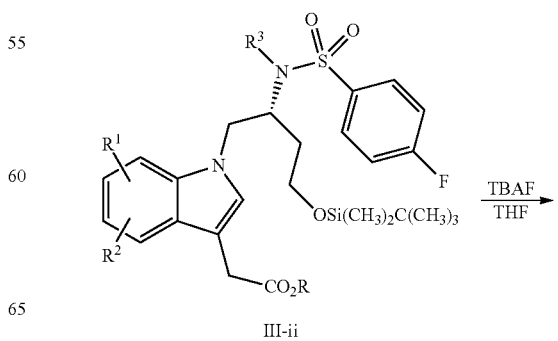

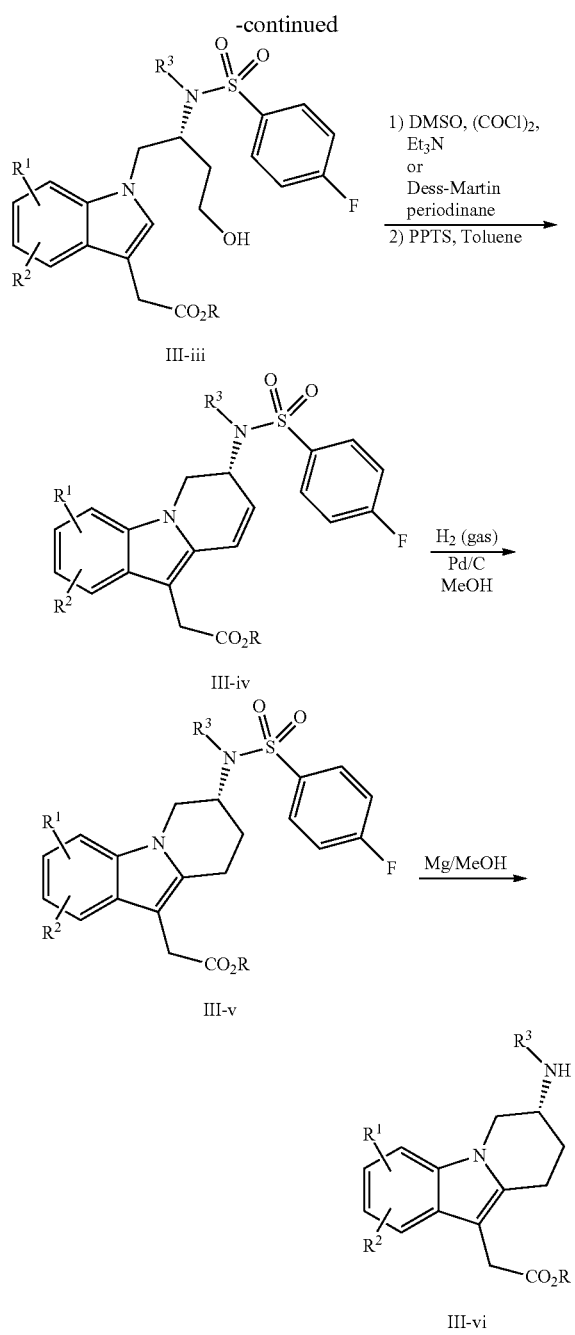

R³' = a R³ group other than H such as methyl
R = lower alkyl (methyl, ethyl, propyl, etc.)

Compounds of formula I can be prepared according to the procedures described in the Schemes and Examples herein, using appropriate materials and are further exemplified by the following specific examples. The compounds exemplified are not, however, to be construed as limiting the scope of the invention in any manner. The examples further illustrate details for the preparation of the compounds of the present invention. Those skilled in the art will readily understand that known variations of protecting groups, of reagents, as well as of the conditions and processes of the following preparative procedures, can be used to prepare these compounds. It is also understood that whenever a chemical reagent is not commercially available, such a chemical reagent can be readily prepared by those skilled in the art by either following or adapting known methods described in the literature. All temperatures are degrees Celsius unless otherwise noted. Mass spectra (MS) were measured either by electrospray ion-mass spectroscopy (ESMS) or by atmospheric pressure chemical ionization mass spectroscopy (APCI).

EXAMPLE 1

{(7R)-7-[[2-(4-Fluorophenyl)propanoyl](methyl)amino]-6,7,8,9-tetrahydropyrido[1,2-a]indol-10-yl}acetic acid

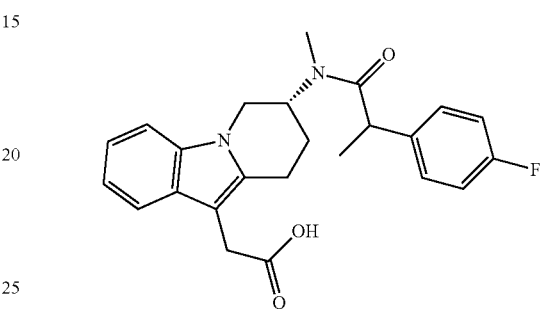

Step 1: Propyl [(7R)-7-(methylamino)-6,7,8,9-tetrahydropyrido[1,2-a]indol-10-yl]acetate Propyl [(7R)-7-amino-6,7,8,9-tetrahydropyrido[1,2-a]indol-10-yl]acetate (2.5 g) and TEA (1.4 mL) were dissolved in 87 mL MeOH. Boc₂O (2.1 g) was added in 10 mL MeOH, and the mixture was stirred for 2 h. The solvent was removed and propyl {(7R)-7-[(tert-butoxycarbonyl)amino]-6,7,8,9-tetrahydropyrido[1,2-a]indol-10-yl}acetate was purified on silica gel (ethyl acetate/hexanes). Propyl {(7R)-7-[(tert-butoxycarbonyl)amino]-6,7,8,9-tetrahydropyrido[1,2-a]indol-10-yl}acetate (3.15 g) was dissolved in DMF (81 mL). The mixture was cooled in an ice bath and MeI (3.47 g) was added followed by NaH (342 mg, 60% w/w in mineral oil). The ice bath was removed after 0.5 h, and the mixture was stirred for 1 h at RT. The reaction was quenched with ½ (sat.) aqueous ammonium chloride. Work up consisted of extraction of the aqueous layer with ether (2×). The combined organic fractions were washed with water and brine, then dried (MgSO₄). The solvent was evaporated under reduced pressure and propyl {(7R)-7-[(tert-butoxycarbonyl)(methyl)amino]-6,7,8,9-tetrahydropyrido[1,2-a]indol-10-yl}acetate was purified on silica gel (ethyl acetate/hexanes). {(7R)-7-[(tert-butoxycarbonyl)-(methyl)amino]-6,7,8,9-tetrahydropyrido[1,2-a]indol-10-yl}acetate and anisole (2.2 g) were dissolved in 66 mL DCM. 66 mL of TFA was added and the mixture was stirred for 1 h. The mixture was then stripped several times with toluene. Work up consisted of extraction with dichloromethane (3×) from aqueous sodium carbonate. The combined organic fractions were washed with brine and dried (MgSO₄). The solvent was evaporated under reduced pressure and propyl [(7R)-7-(methylamino)-6,7,8,9-tetrahydropyrido[1,2-a]indol-10-yl]acetate was obtained after purification on silica gel. (MeOH/DCM).

Step 2: Preparation of 2-(4-fluorophenyl)propanoic acid

Methyl (4-fluorophenyl)acetate (0.5 g) was dissolved in DMF (81 mL). The mixture was cooled in an ice bath and NaH (131 mg, 60% w/w in mineral oil) was added. The mixture was stirred for 1 h at RT and again cooled in an ice bath before the addition of MeI (633 mg). The mixture was warmed to RT and, the reaction was quenched with ½ (sat.)

aqueous ammonium chloride. Work up consisted of extraction of the aqueous layer with ether (2×). The combined organic fractions were washed with water and brine, then dried (MgSO₄). The solvent was evaporated under reduced pressure and methyl 2-(4-fluorophenyl)propanoate was purified on silica gel (ethyl acetate/hexanes). Methyl 2-(4-fluorophenyl)propanoate (420 mg) was dissolved in 12 mL THF and 6 mL MeOH. 6 mL of KOH (2M) was added and the mixture was stirred for 2 h at RT. Water was added and the organic solvents were removed. The base was quenched with icy hydrochloric acid (1N), DCM was added and the phases separated with a phase separator. The solvent was removed under reduced pressure to provide the title compound.

Step 3: (Method A)

2-(4-Fluorophenyl)propanoic acid. (33 mg) and HATU (76 mg) were dissolved in DMF (1.3 mL). DIPEA (87 μL, 0.315 mmol) was added and the mixture was stirred for 1 min before the addition of propyl [(7R)-7-(methylamino)-6,7,8,9-tetrahydropyrido[1,2-a]indol-10-yl]acetate (50 mg) in 1 mL DMF. The reaction mixture was stirred for 2 h. The solvent was removed under vacuum and the residue was purified on silica gel (ethyl acetate/hexanes). The resulting diastereoisomers were separated on a Chiralpak AD column (20% iPrOH/Hexanes, 0.25% HCOOH). The propyl esters were hydrolysed to their corresponding acids using a procedure analogous to the one described in Step 2. MS (+ESI) m/z: 409.

EXAMPLE 2

{(7R)-7-[[(4-fluorophenyl)acetyl](methyl)amino]-6,7,8,9-tetrahydropyrido[1,2-a]indol-10-yl}acetic acid

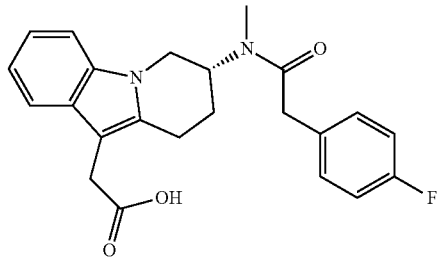 [SMILES: CN(C(=O)Cc1ccc(F)cc1)[C@@H]1CCc2c(CC(=O)O)c3ccccc3n2C1]

(Method B)

Propyl [(7R)-7-(methylamino)-6,7,8,9-tetrahydropyrido[1,2-a]indol-10-yl]acetate (Example 1) (20.0 mg) was dissolved in DCM (2.0 mL) then DMAP (0.449 mg), (4-fluorophenyl)acetyl chloride (16.0 μL) and triethylamine (10.24 μL) were added to the solution under nitrogen atmosphere. The reaction mixture was stirred at room temperature for 2 h then quenched with ½(sat.) aqueous ammonium chloride. DCM (4.0 mL) was added and the two phases were separated by using a phase separator. The solvent was evaporated under reduced pressure and the residue was purified by column chromatography on silica gel (ethyl acetate/hexanes). The resultant material was dissolved in THF (2.0 mL) and MeOH (1.0 mL) then sodium hydroxide (1.32 mL) was added to the solution. The reaction was stirred for 2.5 h at room temperature and then quenched with HCl (1N). DCM was added and the two phases were separated with a phase separator. The organic layers were evaporated under reduced pressure to provide the title compound. MS (+ESI) m/z: 395.2.

EXAMPLE 3

((7R)-7-{(4-fluorobenzyl)[(4-fluorophenyl)acetyl]amino}-6,7,8,9-tetrahydropyrido[1,2-a]indol-10-yl) acetic acid

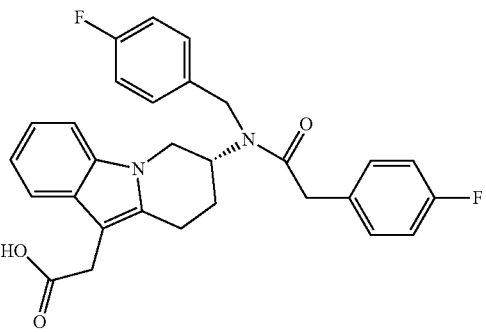 [SMILES: O=C(O)Cc1c2n(c3ccccc13)C[C@H](N(Cc1ccc(F)cc1)C(=O)Cc1ccc(F)cc1)CC2]

4-Fluorobenzaldehyde (43.0 μL) was dissolved in MeOH (3.0 mL) and then propyl [(7R)-7-amino-6,7,8,9-tetrahydropyrido[1,2-a]indol-10-yl]acetate (231 mg) in MeOH (2.0 mL), sodium cyanoborohydride (50.6 mg) and acetic acid (92.0 μL) were added. The reaction mixture was stirred for overnight at room temperature then quenched with NaOH (1N). The aqueous phase was extracted with EtOAc. The organic layers were washed with brine, dried over magnesium sulfate, filtered and the solvent was evaporated under reduced pressure. The residue was purified by column chromatography on silica gel (ethyl acetate/hexanes). The resulting benzylamine (48.0 mg) was dissolved in DCM (2.0 mL) and then DMAP (0.743 mg), (4-fluorophenyl)acetyl chloride (32.8 mg) and triethylamine (17.0 μL) were added to the solution under nitrogen atmosphere. The reaction mixture was stirred at room temperature for 2 h then quenched with ½(sat.) aqueous ammonium chloride. DCM (4.0 mL) was added and the two phases were separated by using a phase separator. The solvent was evaporated under reduced pressure and the residue was purified by column chromatography on silica gel (ethyl acetate/hexanes) to give the title compound as a yellow oil. The resultant material was dissolved in THF (4.0 mL) and MeOH (2.0 mL) then NaOH (0.283 mL, 1N) were added to the solution. The reaction was stirred for 2.5 h at room temperature and then quenched with HCl (1N). DCM was added and the two phases were separated with a phase separator. The organic layers were evaporated under reduced pressure to provide the title compound. MS (+ESI) m/z: 489.

EXAMPLE 4

[(7R)-7-({[1-(4-fluorophenyl)cyclopentyl]carbonyl}amino)-6,7,8,9-tetrahydropyrido[1,2-a]indol-10-yl]acetic acid

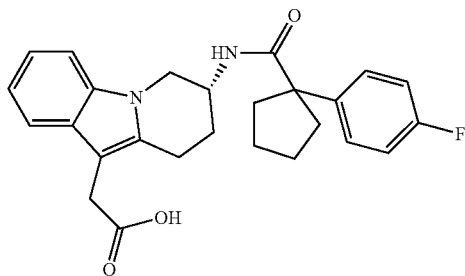 [SMILES: O=C(O)Cc1c2n(c3ccccc13)C[C@H](NC(=O)C1(c3ccc(F)cc3)CCCC1)CC2]

The title compound was prepared using analogous procedures described in Example 1 (Method A) from 1-(4-fluorophenyl)cyclopentanecarboxylic acid and propyl [(7R)-7-amino-6,7,8,9-tetrahydropyrido[1,2-a]indol-10-yl]acetate. MS (+ESI) m/z: 435.

EXAMPLE 5

{(7R)-7-[{[1-(4-fluorophenyl)cyclopentyl]carbonyl}(methyl)amino]-6,7,8,9-tetrahydropyrido[1,2-a]indol-10-yl}acetic acid

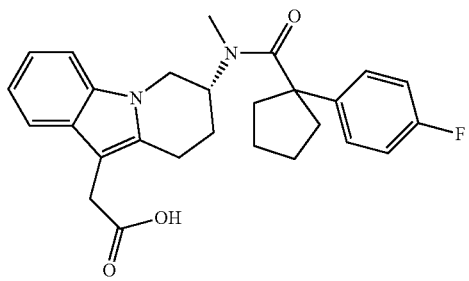 [SMILES: CN(C(=O)C1(c2ccc(F)cc2)CCCC1)[C@@H]1CCc2c(CC(=O)O)c3ccccc3n2C1]

The title compound was prepared using analogous procedures described in Example 1 (Method A) from 1-(4-fluorophenyl)cyclopentanecarboxylic acid and propyl [(7R)-7-(methylamino)-6,7,8,9-tetrahydropyrido[1,2-a]indol-10-yl]acetate. MS (+ESI) m/z: 449.

EXAMPLE 6

{(7R)-7-[[2-(4-fluorophenyl)-2-methylpropanoyl](methyl)amino]-6,7,8,9-tetrahydropyrido[1,2-a]indol-10-yl}acetic acid

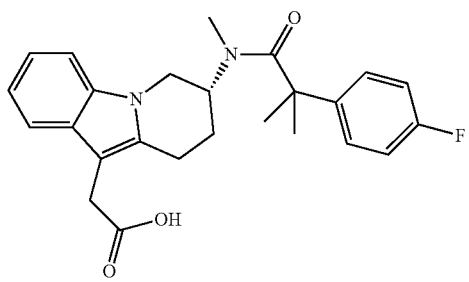 [SMILES: CN(C(=O)C(C)(C)c1ccc(F)cc1)[C@@H]1CCc2c(CC(=O)O)c3ccccc3n2C1]

The title compound was prepared using analogous procedures described in Example 1 (Method A) from 2-(4-fluorophenyl)-2-methylpropanoic acid and propyl [(7R)-7-(methylamino)-6,7,8,9-tetrahydropyrido[1,2-a]indol-10-yl]acetate. MS (+ESI) m/z: 423.

EXAMPLE 7

{(7R)-7-[[(2,4-difluorophenyl)acetyl](methyl)amino]-6,7,8,9-tetrahydropyrido[1,2-a]indol-10-yl}acetic acid

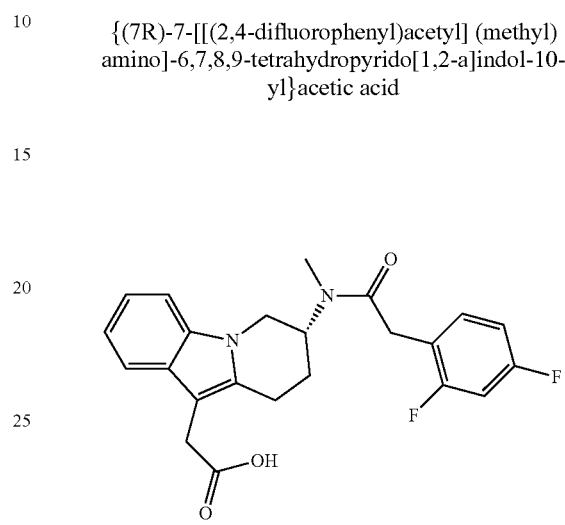

The title compound was prepared using analogous procedures described in Example 1 (Method A) from (2,4-difluorophenyl)acetic acid and propyl [(7R)-7-(methylamino)-6,7,8,9-tetrahydropyrido[1,2-a]indol-10-yl]acetate. MS (+ESI) m/z: 413.

EXAMPLE 8

{(7R)-7-[[(2-chloro-4-fluorophenyl)acetyl](methyl)amino]-6,7,8,9-tetrahydropyrido[1,2-a]indol-10-yl}acetic acid

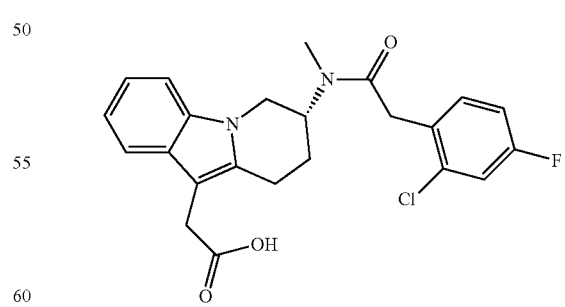

The title compound was prepared using analogous procedures described in Example 1 (Method A) from (2-chloro-4fluorophenyl)acetic acid and propyl [(7R)-7-(methylamino)-6,7,8,9-tetrahydropyrido[1,2-a]indol-10-yl]acetate. MS (+ESI) m/z: 429.

EXAMPLE 9

{(7R)-7-[[(3-chloro-4-fluorophenyl)acetyl](methyl)amino]-6,7,8,9-tetrahydropyrido[1,2-a]indol-10-yl}acetic acid

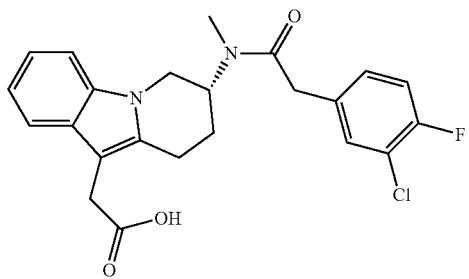 [SMILES: CN(C(=O)Cc1ccc(F)c(Cl)c1)[C@@H]1CCc2c(CC(=O)O)c3ccccc3n2C1]

The title compound was prepared using analogous procedures described in Example 1 (Method A) from (3-chloro-4-fluorophenyl)acetic acid and propyl [(7R)-7-(methylamino)-6,7,8,9-tetrahydropyrido[1,2-a]indol-10-yl]acetate. MS (+ESI) m/z: 429.

EXAMPLE 10

{(7R)-7-[{[4-fluoro-2-(trifluoromethyl)phenyl]acetyl}(methyl)amino]-6,7,8,9-tetrahydropyrido[1,2-a]indol-10-yl}acetic acid

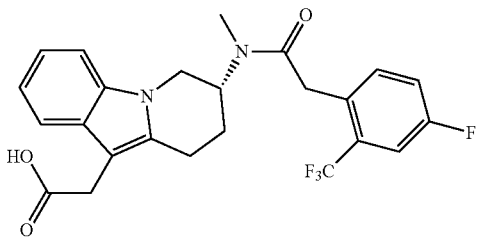 [SMILES: CN(C(=O)Cc1ccc(F)cc1C(F)(F)F)[C@@H]1CCc2c(CC(=O)O)c3ccccc3n2C1]

The title compound was prepared using analogous procedures described in Example 1 (Method A) from [4-fluoro-2-(trifluoromethyl)phenyl]acetic acid and propyl [(7R)-7-(methylamino)-6,7,8,9-tetrahydropyrido[1,2-a]indol-10-yl]acetate. MS (+ESI) m/z: 463.

EXAMPLE 11

{(7R)-7-[{[4-fluoro-3-(trifluoromethyl)phenyl]acetyl}(methyl)amino]-6,7,8,9-tetrahydropyrido[1,2-a]indol-10-yl}acetic acid

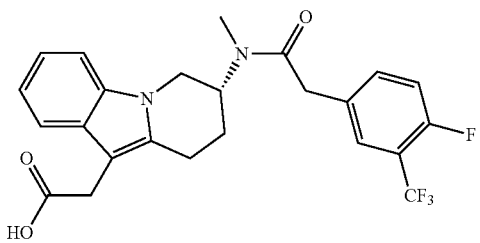 [SMILES: CN(C(=O)Cc1ccc(F)c(C(F)(F)F)c1)[C@@H]1CCc2c(CC(=O)O)c3ccccc3n2C1]

The title compound was prepared using analogous procedures described in Example 1 (Method A) from [4-fluoro-3-(trifluoromethyl)phenyl]acetic acid and propyl [(7R)-7-(methylamino)-6,7,8,9-tetrahydropyrido[1,2-a]indol-10-yl]acetate. MS (+ESI) m/z: 463.

EXAMPLE 12

{(7R)-7-[(2,3-dihydro-1H-inden-1-ylcarbonyl)(methyl)amino]-6,7,8,9-tetrahydropyrido[1,2-a]-indol-10-yl}acetic acid

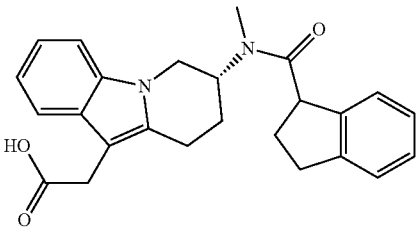 [SMILES: CN(C(=O)C1CCc2ccccc21)[C@@H]1CCc2c(CC(=O)O)c3ccccc3n2C1]

The title compound was prepared using analogous procedures described in Example 1 (Method A) from indane-1-carboxylic acid and propyl [(7R)-7-(methylamino)-6,7,8,9-tetrahydropyrido[1,2-a]indol-10-yl]acetate. MS (+ESI) m/z: 403.

EXAMPLE 13

{(7R)-7-[[4-(difluoromethyl)-3-iodobenzoyl](methyl)amino]-6,7,8,9-tetrahydropyrido[1,2-a]-indol-10-yl}acetic acid

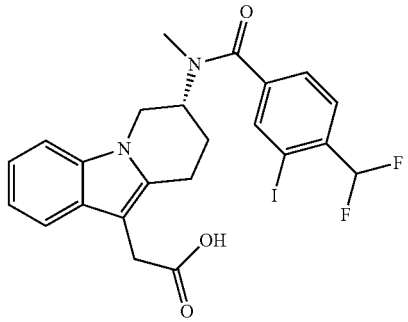 [SMILES: CN(C(=O)c1ccc(C(F)F)c(I)c1)[C@@H]1CCc2c(CC(=O)O)c3ccccc3n2C1]

The title compound was prepared using analogous procedures described in Example 1 (Method A) from 4-(difluoromethyl)-3-iodobenzoic acid and propyl [(7R)-7-(methylamino)-6,7,8,9-tetrahydropyrido[1,2-a]indol-10-yl]acetate. MS (+ESI) m/z: 539.

EXAMPLE 14

{(7R)-7-[[(2-(2-bromo-4-fluorophenyl)propanoyl](methyl)amino]-6,7,8,9-tetrahydropyrido[1,2-a]indol-10-yl}acetic acid

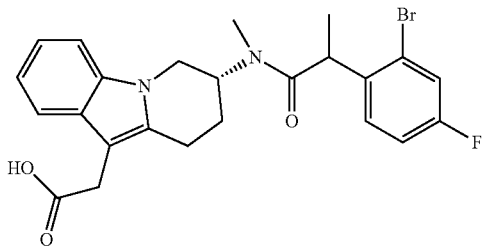

The title compound was prepared using analogous procedures described in Example 1 (Method A) from 2-(2-bromo- 4-fluorophenyl)propanoic acid and propyl [(7R)-7-(methylamino)-6,7,8,9-tetrahydropyrido[1,2-a]indol-10-yl]acetate. MS (+ESI) m/z: 487.

EXAMPLE 15

{(7R)-7-[(4-fluorobenzoyl)(methyl)amino]-6,7,8,9-tetrahydropyrido[1,2-a]indol-10-yl}acetic acid

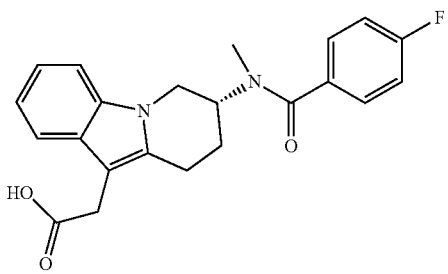 [SMILES: CN(C(=O)c1ccc(F)cc1)[C@@H]1CCc2c(CC(=O)O)c3ccccc3n2C1]

The title compound was prepared using analogous procedures described in Example 2 (Method B) from 4-fluorobenzoyl chloride and propyl [(7R)-7-(methylamino)-6,7,8,9-tetrahydropyrido[1,2-a]indol-10-yl]acetate. MS (+ESI) m/z: 381.

EXAMPLE 16

{(7R)-7-[(cyclopentylcarbonyl)(methyl)amino]-6,7,8,9-tetrahydropyrido[1,2-a]indol-10-yl}acetic acid

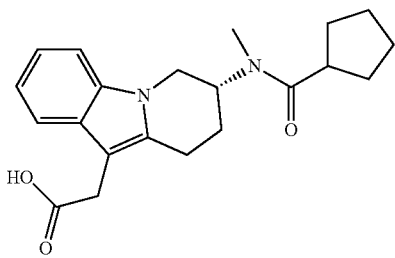 [SMILES: CN(C(=O)C1CCCC1)[C@@H]1CCc2c(CC(=O)O)c3ccccc3n2C1]

The title compound was prepared using analogous procedures described in Example 2 (Method B) from cyclopentanecarboxylic acid and propyl [(7R)-7-(methylamino)-6,7,8,9-tetrahydropyrido[1,2-a]indol-10-yl]acetate. MS (+ESI) m/z: 355.

EXAMPLE 17

{(7R)-7-[(cyclopropylcarbonyl)(methyl)amino]-6,7,8,9-tetrahydropyrido[1,2-a]indol-10-yl}acetic acid

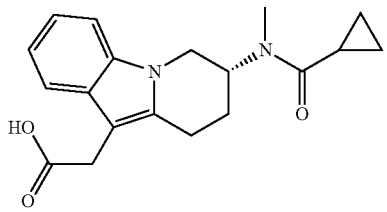 [SMILES: CN(C(=O)C1CC1)[C@@H]1CCc2c(CC(=O)O)c3ccccc3n2C1]

The title compound was prepared using analogous procedures described in Example 2 (Method B) from cyclopropanecarboxylic acid and propyl [(7R)-7-(methylamino)-6,7,8,9-tetrahydropyrido[1,2-a]indol-10-yl]acetate. MS (+ESI) m/z: 327.

EXAMPLE 18

((7R)-7-{methyl [(5-methylisoxazol-3-yl)carbonyl]amino}-6,7,8,9-tetrahydropyrido[1,2-a]indol-10-yl)acetic acid

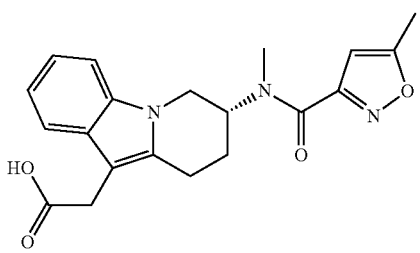 [SMILES: Cc1cc(C(=O)N(C)[C@@H]2CCc3c(CC(=O)O)c4ccccc4n3C2)no1]

The title compound was prepared using analogous procedures described in Example 2 (Method B) from 5-methylisoxazole-3-carbonyl chloride and propyl [(7R)-7-(methylamino)-6,7,8,9-tetrahydropyrido[1,2-a]indol-10-yl]acetate. MS (+ESI) m/z: 368.

EXAMPLE 19

(7R)-7-[[(4-chlorophenyl)acetyl] (methyl)amino]-6,7,8,9-tetrahydropyrido[1,2-a]indol-10-yl}-acetic acid

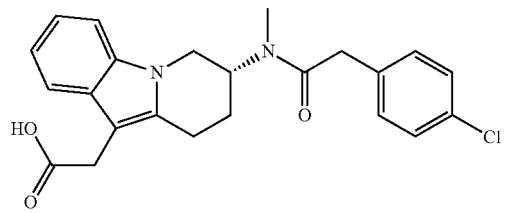 [SMILES: CN(C(=O)Cc1ccc(Cl)cc1)[C@@H]1CCc2c(CC(=O)O)c3ccccc3n2C1]

The title compound was prepared using analogous procedures described in Example 2 (Method B) from (4-chlorophenyl)acetyl chloride and propyl [(7R)-7-(methylamino)-6,7,8,9-tetrahydropyrido[1,2-a]indol-10-yl]acetate. MS (+ESI) m/z: 411.

EXAMPLE 20

{(7R)-7-[{[1-(4-chlorophenyl)cyclopentyl]carbonyl}(methyl)amino]-6,7,8,9-tetrahydropyrido[1,2-a]indol-10-yl}acetic acid

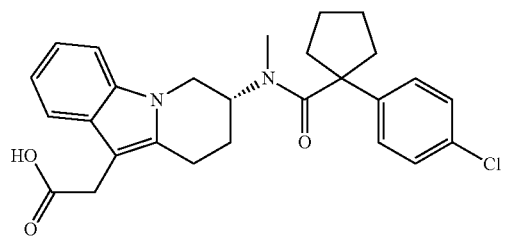 [SMILES: CN(C(=O)C1(c2ccc(Cl)cc2)CCCC1)[C@@H]1CCc2c(CC(=O)O)c3ccccc3n2C1]

The title compound was prepared using analogous procedures described in Example 2 (Method B) from 1-(4-chlorophenyl)cyclopentanecarbonyl chloride and propyl [(7R)-7-(methylamino)-6,7,8,9-tetrahydropyrido[1,2-a]indol-10-yl]acetate. MS (+ESI) m/z: 487.

EXAMPLE 21

{(7R)-7-[[(4-methoxyphenyl)acetyl](methyl)amino]-6,7,8,9-tetrahydropyrido[1,2-a]indol-10-yl}-acetic acid

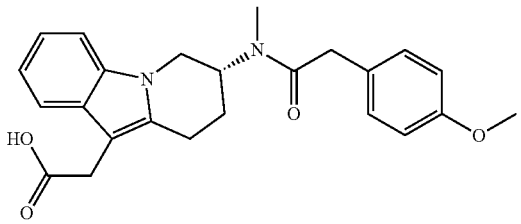 [SMILES: COc1ccc(CC(=O)N(C)[C@@H]2CCc3c(CC(=O)O)c4ccccc4n3C2)cc1]

The title compound was prepared using analogous procedures described in Example 2 (Method B) from (4-methoxyphenyl)acetyl chloride and propyl [(7R)-7-(methylamino)-6,7,8,9-tetrahydropyrido[1,2-a]indol-10-yl]acetate. MS (+ESI) m/z: 407.

EXAMPLE 22

{(7R)-7-[methyl(phenoxyacetyl)amino]-6,7,8,9-tetrahydropyrido[1,2-a]indol-10-yl}acetic acid

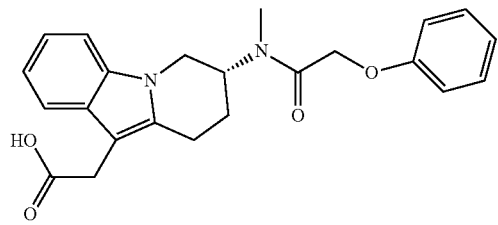 [SMILES: CN(C(=O)COc1ccccc1)[C@@H]1CCc2c(CC(=O)O)c3ccccc3n2C1]

The title compound was prepared using analogous procedures described in Example 2 (Method B) from phenoxyacetyl chloride and propyl [(7R)-7-(methylamino)-6,7,8,9-tetrahydropyrido[1,2-a]indol-10-yl]acetate. MS (+ESI) m/z: 393.

EXAMPLE 23

{(7R)-7-[methyl(phenylacetyl)amino]-6,7,8,9-tetrahydropyrido[1,2-a]indol-10-yl}acetic acid

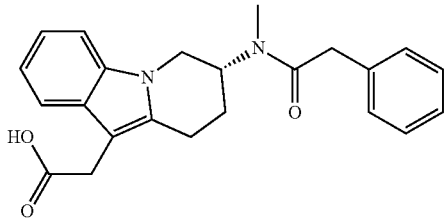 [SMILES: CN(C(=O)Cc1ccccc1)[C@@H]1CCc2c(CC(=O)O)c3ccccc3n2C1]

The title compound was prepared using analogous procedures described in Example 2 (Method B) from phenylacetyl chloride and propyl [(7R)-7-(methylamino)-6,7,8,9-tetrahydropyrido[1,2-a]indol-10-yl]acetate. MS (+ESI) m/z: 377.

EXAMPLE 24

{(7R)-7-[methyl(2-naphthoyl)amino]-6,7,8,9-tetrahydropyrido[1,2-a]indol-10-yl}acetic acid

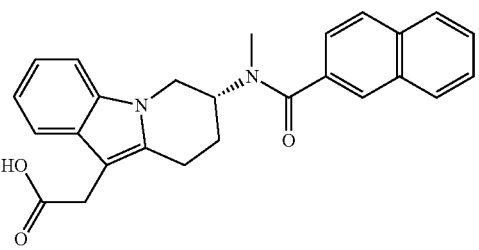 [SMILES: CN(C(=O)c1ccc2ccccc2c1)[C@@H]1CCc2c(CC(=O)O)c3ccccc3n2C1]

The title compound was prepared using analogous procedures described in Example 2 (Method B) from 2-naphthoyl chloride and propyl [(7R)-7-(methylamino)-6,7,8,9-tetrahydropyrido[1,2-a]indol-10-yl]acetate. MS (+ESI) m/z: 413.

EXAMPLE 25

{(7R)-7-[[(3,4-difluorophenyl)acetyl](methyl)amino]-6,7,8,9-tetrahydropyrido[1,2-a]indol-10-yl}acetic acid

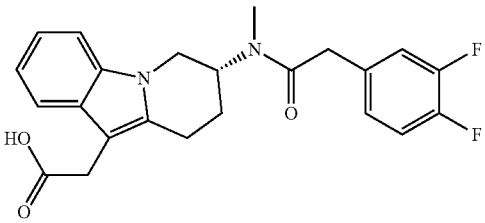 [SMILES: CN(C(=O)Cc1ccc(F)c(F)c1)[C@@H]1CCc2c(CC(=O)O)c3ccccc3n2C1]

The title compound was prepared using analogous procedures described in Example 2 (Method B) from (3,4-difluorophenyl)acetyl chloride and propyl [(7R)-7-(methylamino)-6,7,8,9-tetrahydropyrido[1,2-a]indol-10-yl]acetate. MS (+ESI) m/z: 413.

EXAMPLE 26

{(7R)-7-[(2,2-dimethyl-3-phenylpropanoyl)(methyl)amino]-6,7,8,9-tetrahydropyrido[1,2-a]indol-10-yl}acetic acid

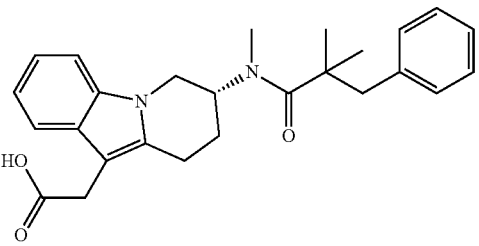 [SMILES: CN(C(=O)C(C)(C)Cc1ccccc1)[C@@H]1CCc2c(CC(=O)O)c3ccccc3n2C1]

The title compound was prepared using analogous procedures described in Example 2 (Method B) from 2,2-dimethyl- 3-phenylpropanoyl chloride and propyl [(7R)-7-(methylamino)-6,7,8,9-tetrahydropyrido[1,2-a]indol-10-yl]acetate. MS (+ESI) m/z: 419.

EXAMPLE 27

[(7R)-7-(methyl{[4-(trifluoromethyl)phenyl]acetyl}amino)-6,7,8,9-tetrahydropyrido[1,2-a]indol-10-yl]acetic acid

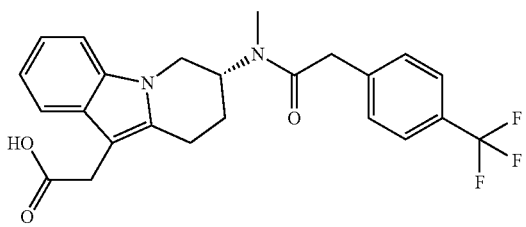 [SMILES: CN(C(=O)Cc1ccc(C(F)(F)F)cc1)[C@@H]1CCc2c(CC(=O)O)c3ccccc3n2C1]

The title compound was prepared using analogous procedures described in Example 1 (Method A) from [4-(trifluoromethyl)phenyl]acetic acid and propyl [(7R)-7-(methylamino)-6,7,8,9-tetrahydropyrido[1,2-a]indol-10-yl]acetate. MS (+ESI) m/z: 445.

EXAMPLE 28

{(7R)-7-[methyl(1-naphthylacetyl)amino]-6,7,8,9-tetrahydropyrido[1,2-a]indol-10-yl}acetic acid

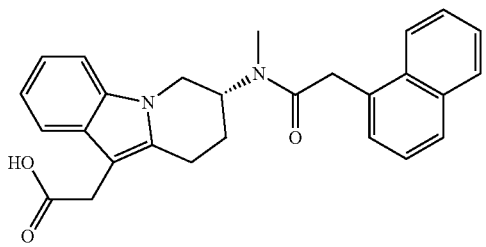 [SMILES: CN(C(=O)Cc1cccc2ccccc12)[C@@H]1CCc2c(CC(=O)O)c3ccccc3n2C1]

The title compound was prepared using analogous procedures described in Example 1 (Method A) from 1-naphthylacetic acid and propyl [(7R)-7-(methylamino)-6,7,8,9-tetrahydropyrido[1,2-a]indol-10-yl]acetate. MS (+ESI) m/z: 427

EXAMPLE 29

{(7R)-7-[methyl(3-phenylpropanoyl)amino]-6,7,8,9-tetrahydropyrido[1,2-a]indol-10-yl}acetic acid

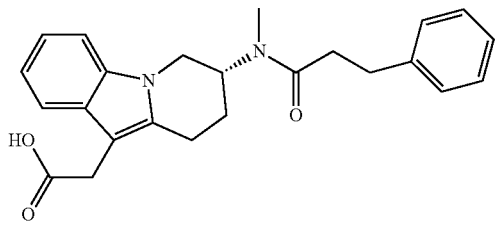

The title compound was prepared using analogous procedures described in Example 1 (Method A) from 3-phenylpropanoic acid. and propyl [(7R)-7-(methylamino)-6,7,8,9-tetrahydropyrido[1,2-a]indol-10-yl]acetate. MS (+ES I) m/z: 391.

EXAMPLE 30

((7R)-7-{methyl [2-phenylpropanoyl]amino}-6,7,8,9-tetrahydropyrido[1,2-a]indol-10-yl)acetic acid

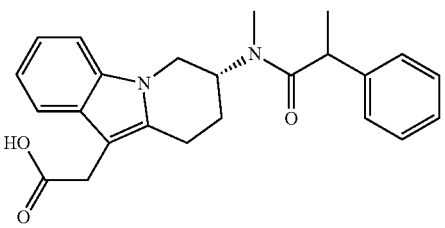

The title compound was prepared using analogous procedures described in Example 1 (Method A) from hydratropic acid and propyl [(7R)-7-(methylamino)-6,7,8,9-tetrahydropyrido[1,2-a]indol-10-yl]acetate. MS (+ESI) m/z: 391.

EXAMPLE 31

{(7R)-7-[{[1-(4-fluorophenyl)cyclopropyl]carbonyl}(methyl)amino]-6,7,8,9-tetrahydropyrido[1,2-a]indol-10-yl}acetic acid

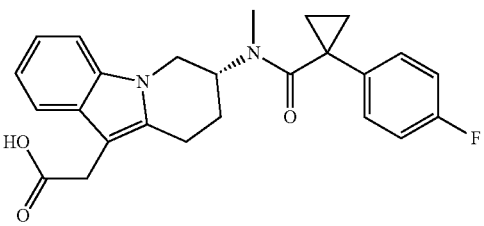 [SMILES: CN(C(=O)C1(c2ccc(F)cc2)CC1)[C@@H]1CCc2c(CC(=O)O)c3ccccc3n2C1]

The title compound was prepared using analogous procedures described in Example 1 (Method A) from 1-(4-fluorophenyl)cyclopropanecarboxylic acid and propyl [(7R)-7-(methylamino)-6,7,8,9-tetrahydropyrido[1,2-a]indol-10-yl]acetate. MS (+ESI) m/z: 321.

EXAMPLE 32

{(7R)-7-[{[1-(4-fluorophenyl)cyclobutyl]carbonyl}(methyl)amino]-6,7,8,9-tetrahydropyrido[1,2-a]indol-10-yl}acetic acid

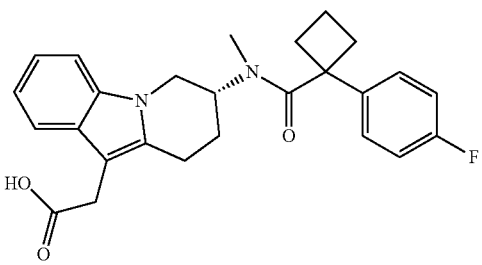 [SMILES: CN(C(=O)C1(c2ccc(F)cc2)CCC1)[C@@H]1CCc2c(CC(=O)O)c3ccccc3n2C1]

The title compound was prepared using analogous procedures described in Example 1 (Method A) from 1-(4-fluorophenyl)cyclobutanecarboxylic acid and propyl [(7R)-7-(methylamino)-6,7,8,9-tetrahydropyrido[1,2-a]indol-10-yl]acetate. MS (+ESI) m/z: 435.

EXAMPLE 33

{(7R)-7-[[2-(4-fluorophenyl)-2-piperidin-1-ylacetyl](methyl)amino]-6,7,8,9-tetrahydropyrido[1,2-a]indol-10-yl}acetic acid

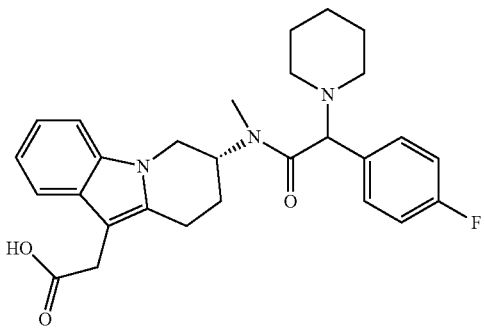 [SMILES: CN(C(=O)C(c1ccc(F)cc1)N1CCCCC1)[C@@H]1CCc2c(CC(=O)O)c3ccccc3n2C1]

The title compound was prepared using analogous procedures described in Example 1 (Method A) from (4-fluorophenyl)(piperidin-1-yl)acetic acid and propyl [(7R)-7-(methylamino)-6,7,8,9-tetrahydropyrido[1,2-a]indol-10-yl]acetate. MS (+ESI) m/z: 478.

EXAMPLE 34

{(7R)-7-[[(2-bromo-4-fluorophenyl)acetyl](methyl)amino]-6,7,8,9-tetrahydropyrido[1,2-a]indol-10-yl}acetic acid

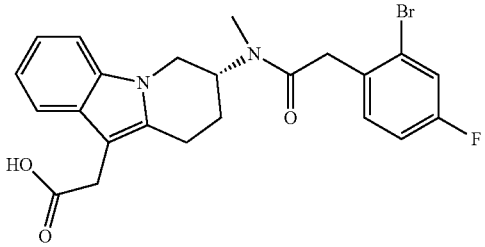 [SMILES: CN(C(=O)Cc1ccc(F)cc1Br)[C@@H]1CCc2c(CC(=O)O)c3ccccc3n2C1]

The title compound was prepared using analogous procedures described in Example 1 (Method A) from (2-bromo-4-fluorophenyl)acetic acid and propyl [(7R)-7-(methylamino)-6,7,8,9-tetrahydropyrido[1,2-a]indol-10-yl]acetate. MS (+ESI) m/z: 473.

EXAMPLE 35

{(7R)-7-[{[1-(4-fluorophenyl)-2,2-dimethylcyclopropyl]carbonyl}(methyl)amino]-6,7,8,9-tetrahydropyrido[1,2-a]indol-10-yl}acetic acid

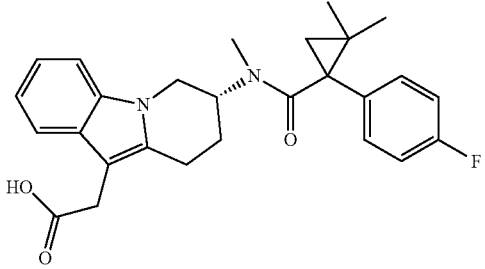 [SMILES: CN(C(=O)C1(c2ccc(F)cc2)CC1(C)C)[C@@H]1CCc2c(CC(=O)O)c3ccccc3n2C1]

The title compound was prepared using analogous procedures described in Example 1 (Method B) 1-(4-fluorophenyl)-2,2-dimethylcyclopropanecarboxylic acid and propyl [(7R)-7-(methylamino)-6,7,8,9-tetrahydropyrido[1,2-a]indol-10-yl]acetate. MS (+ESI) m/z: 449.

EXAMPLE 36

{(7R)-7-[[-2-methoxy-2-phenylacetyl](methyl)amino]-6,7,8,9-tetrahydropyrido[1,2-a]indol-10-yl}acetic acid

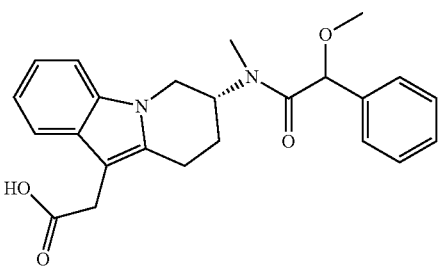 [SMILES: COC(C(=O)N(C)[C@@H]1CCc2c(CC(=O)O)c3ccccc3n2C1)c1ccccc1]

The title compound was prepared using analogous procedures described in Example 1 (Method A) from methoxy(phenyl)acetic acid and propyl [(7R)-7-(methylamino)-6,7,8,9-tetrahydropyrido[1,2-a]indol-10-yl]acetate. MS (+ESI) m/z: 407.

EXAMPLE 37

{(7R)-7-[Methyl-(2-thiophen-2-yl-acetyl)-amino]-6,7,8,9-tetrahydro-pyrido[1,2-a]indol-10-yl}-acetic acid

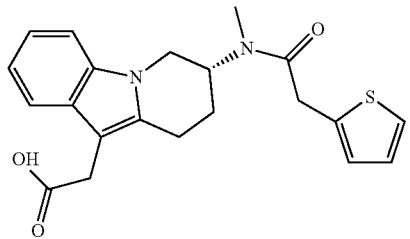 [SMILES: CN(C(=O)Cc1cccs1)[C@@H]1CCc2c(CC(=O)O)c3ccccc3n2C1]

The title compound was prepared using analogous procedures described in Example 1 (Method A) from thiophen-2-yl acetic acid and propyl [(7R)-7-(methylamino)-6,7,8,9-tetrahydropyrido[1,2-a]indol-10-yl]acetate. MS (+ESI) m/z: 383.

EXAMPLE 38

{(7R)-7-[Methyl-(2-thiophen-3-yl-acetyl)-amino]-6,7,8,9-tetrahydro-pyrido[1,2-a]indol-10-yl}-acetic acid

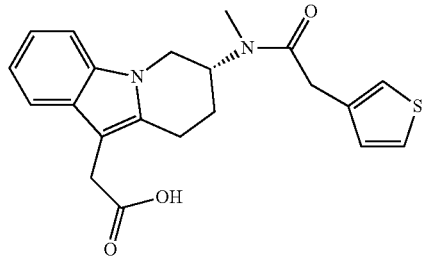 [SMILES: CN(C(=O)Cc1ccsc1)[C@@H]1CCc2c(CC(=O)O)c3ccccc3n2C1]

The title compound was prepared using analogous procedures described in Example 1 (Method A) from thiophen-3-yl acetic acid and propyl [(7R)-7-(methylamino)-6,7,8,9-tetrahydropyrido[1,2-a]indol-10-yl]acetate. MS (+ESI) m/z: 383.

EXAMPLE 39

((7R)-7-{[2,2-Bis-(4-fluoro-phenyl)-acetyl]-methylamino}-6,7,8,9-tetrahydro-pyrido[1,2-a]indol-10-yl)-acetic acid

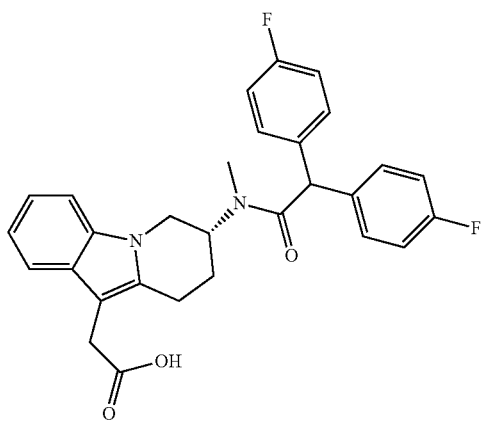 [SMILES: CN(C(=O)C(c1ccc(F)cc1)c1ccc(F)cc1)[C@@H]1CCc2c(CC(=O)O)c3ccccc3n2C1]

The title compound was prepared using analogous procedures described in Example 1 (Method A) from bis(4-fluorophenyl)acetic acid and propyl [(7R)-7-(methylamino)-6,7,8,9-tetrahydropyrido[1,2-a]indol-10-yl]acetate. MS (+ESI) m/z: 489.

EXAMPLE 40

{(7R)-7-[(diphenylacetyl)(methyl)amino]-6,7,8,9-tetrahydropyrido[1,2-a]indol-10-yl}acetic acid

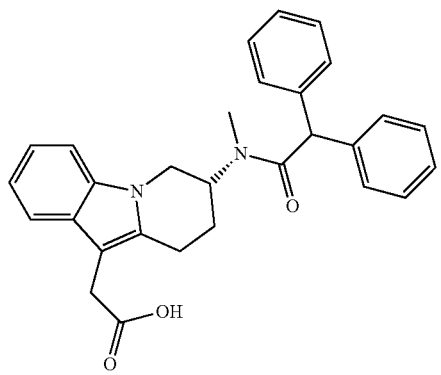

The title compound was prepared using analogous procedures described in Example 2 (Method B) from diphenylacetyl chloride and propyl [(7R)-7-(methylamino)-6,7,8,9-tetrahydropyrido[1,2-a]indol-10-yl]acetate. MS (+ESI) m/z: 453.

EXAMPLE 41

{(7R)-7-[(diphenylacetyl)(methyl)amino]-6,7,8,9-tetrahydropyrido[1,2-a]indol-10-yl}acetic acid

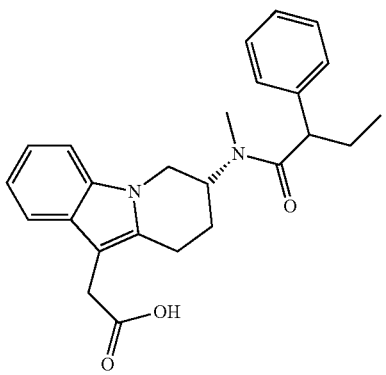

The title compound was prepared using analogous procedures described in Example 2 (Method B) from 2-phenylbutanoyl chloride and propyl [(7R)-7-(methylamino)-6,7,8,9-tetrahydropyrido[1,2-a]indol-10-yl]acetate. MS (+ESI) m/z: 405.

EXAMPLE 42

((7R)-7-{Methyl-[2-(2-methyl-thiazol-4-yl)-acetyl]-amino}-6,7,8,9-tetrahydro-pyrido[1,2-a]indol-10-yl)-acetic acid

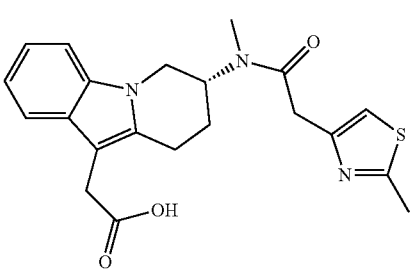 [SMILES: Cc1nc(CC(=O)N(C)[C@@H]2CCc3c(CC(=O)O)c4ccccc4n3C2)cs1]

The title compound was prepared using analogous procedures described in Example 1 (Method A) from (2-methyl-1, 3-thiazol-4-yl)acetic acid and propyl [(7R)-7-(methylamino)-6,7,8,9-tetrahydropyrido[1,2-a]indol-10-yl]acetate. MS (+ESI) m/z: 398.

EXAMPLE 43

((7R)-7-{[2-(3,5-Dimethyl-isoxazol-4-yl)-acetyl]-methyl-amino}-6,7,8,9-tetrahydro-pyrido[1,2-a]indol-10-yl)-acetic acid

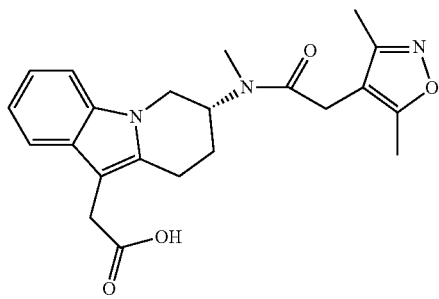 [SMILES: Cc1noc(C)c1CC(=O)N(C)[C@@H]1CCc2c(CC(=O)O)c3ccccc3n2C1]

The title compound was prepared using analogous procedures described in Example 1 (Method A) from (3,5-dimethylisoxazol-4-yl)acetic acid and propyl [(7R)-7-(methylamino)-6,7,8,9-tetrahydropyrido[1,2-a]indol-10-yl]acetate. MS (+ESI) m/z: 396.

EXAMPLE 44

((7R)-7-{[2-Ethyl-2-(4-fluoro-phenyl)-butyryl]-methyl-amino}-6,7,8,9-tetrahydro-pyrido[1,2-a]indol-10-yl)-acetic acid

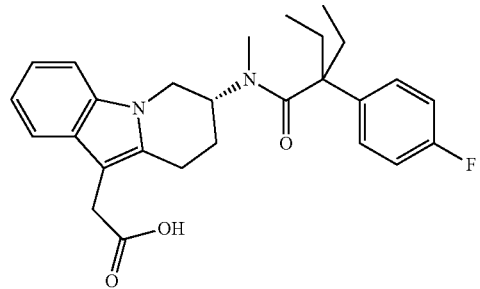 [SMILES: CCC(CC)(C(=O)N(C)[C@@H]1CCc2c(CC(=O)O)c3ccccc3n2C1)c1ccc(F)cc1]

The title compound was prepared using analogous procedures described in Example 2 (Method B) from 2-ethyl-2-(4-fluorophenyl)butanoyl chloride and propyl [(7R)-7-(methylamino)-6,7,8,9-tetrahydropyrido[1,2-a]indol-10-yl]acetate. MS (+ESI) m/z: 451.

EXAMPLE 45

((7R)-7-{[3-Cyclopropyl-2-(4-fluoro-phenyl)-propionyl]-methyl-amino}-6,7,8,9-tetrahydropyrido[1,2-a]indol-10-yl)-acetic acid

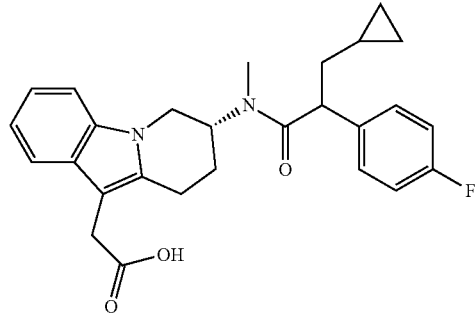 [SMILES: CN(C(=O)C(CC1CC1)c1ccc(F)cc1)[C@@H]1CCc2c(CC(=O)O)c3ccccc3n2C1]

The title compound was prepared using analogous procedures described in Example 1 (Method A) from 3-cyclopropyl-2-(4-fluorophenyl)propanoic acid and propyl [(7R)-7-(methylamino)-6,7,8,9-tetrahydropyrido[1,2-a]indol-10-yl] acetate. MS (+ESI) m/z: 449.

EXAMPLE 46

[(7R)-7-{[(2R)-2-hydroxy-2-phenylpropanoyl](methyl)amino}-6,7,8,9-tetrahydropyrido[1,2-a]indol-10-yl]acetic acid

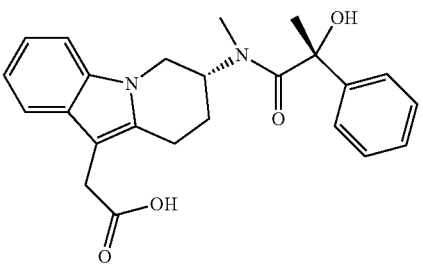 [SMILES: CN(C(=O)[C@](C)(O)c1ccccc1)[C@@H]1CCc2c(CC(=O)O)c3ccccc3n2C1]

The title compound was prepared using analogous procedures described in Example 1 (Method A) from (2R)-2-hydroxy-2-phenylpropanoic acid and propyl [(7R)-7-(methylamino)-6,7,8,9-tetrahydropyrido[1,2-a]indol-10-yl]acetate. MS (+ESI) m/z: 407.

EXAMPLE 47

[(7R)-7-{[(2S)-2-hydroxy-2-phenylpropanoyl](methyl)amino}-6,7,8,9-tetrahydropyrido[1,2-a]-indol-10-yl]acetic acid

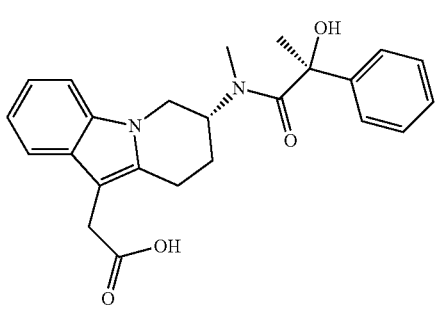 [SMILES: CN(C(=O)[C@@](C)(O)c1ccccc1)[C@@H]1CCc2c(CC(=O)O)c3ccccc3n2C1]

The title compound was prepared using analogous procedures described in Example 1 (Method A) from (2S)-2-hydroxy-2-phenylpropanoic acid and propyl [(7R)-7-(methylamino)-6,7,8,9-tetrahydropyrido[1,2-a]indol-10-yl]acetate. MS (+ES I) m/z: 407.

EXAMPLE 48

((7R)-7-{Ethyl-[1-(4-fluoro-phenyl)-cyclopropanecarbonyl]-amino}-6,7,8,9-tetrahydropyrido[1,2-a]indol-10-yl)-acetic acid

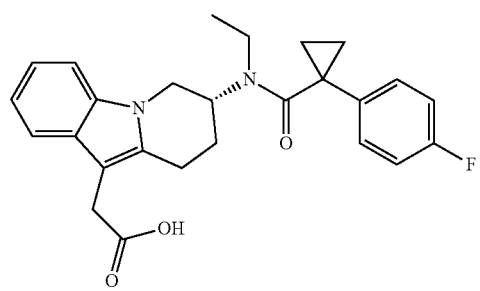 [SMILES: CCN(C(=O)C1(c2ccc(F)cc2)CC1)[C@@H]1CCc2c(CC(=O)O)c3ccccc3n2C1]

Step 1: propyl [(7R)-7-(ethylamino)-6,7,8,9-tetrahydropyrido[1,2-a] indol-10-yl]acetate
This compound was achieved according to the general procedures outlined in Scheme III.
Step 2: ((7R)-7-{Ethyl-[1-(4-fluoro-phenyl)-cyclopropanecarbonyl]-amino}-6,7,8,9-tetrahydro-pyrido[1,2-a]indol-10-yl)-acetic acid The title compound was prepared using analogous procedures described in Example 1 (Method A) from 1-(4-fluorophenyl)cyclopropanecarboxylic acid and propyl [(7R)-7-(ethylamino)-6,7,8,9-tetrahydropyrido[1,2-a]indol-10-yl] acetate. MS (+ESI) m/z: 435.

EXAMPLE 49

[(7R)-7-(methyl {[2-(pyridin-4-yl)cyclopropyl]carbonyl}amino)-6,7,8,9-tetrahydropyrido[1,2-a]indol-10-yl]acetic acid

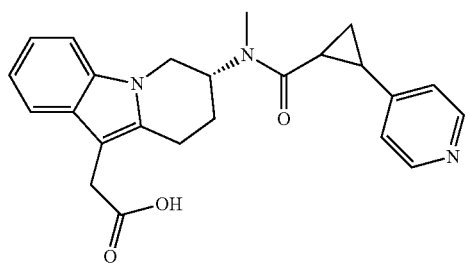 [SMILES: CN(C(=O)C1CC1c1ccncc1)[C@@H]1CCc2c(CC(=O)O)c3ccccc3n2C1]

The title compound was prepared using analogous procedures described in Example 1 (Method A) from 2-(pyridin-4-yl)cyclopropanecarboxylic acid and propyl [(7R)-7-(methylamino)-6,7,8,9-tetrahydropyrido[1,2-a]indol-10-yl] acetate. MS (+ESI) m/z: 404.

EXAMPLE 50

{(7R)-7-[(bicyclo[4.2.0]octa-1,3,5-trien-7-ylcarbonyl)(methyl)amino]-6,7,8,9-tetrahydropyrido[1,2-a]indol-10-yl}acetic acid

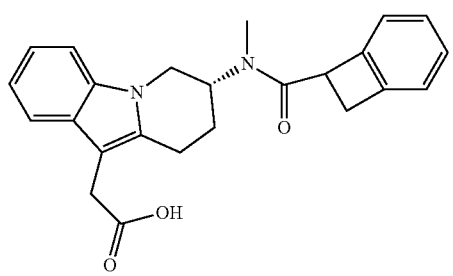 [SMILES: CN(C(=O)C1Cc2ccccc21)[C@@H]1CCc2c(CC(=O)O)c3ccccc3n2C1]

The title compound was prepared using analogous procedures described in Example 1 (Method A) from bicyclo[4.2.0]octa-1,3,5-triene-7-carboxylic acid and propyl [(7R)-

7-(methylamino)-6,7,8,9-tetrahydropyrido[1,2-a]indol-10-yl]acetate. MS (+ESI) m/z: 389.

EXAMPLE 51

{(7R)-7-[(imidazo[1,2-a]pyridin-3-ylacetyl)(methyl)amino]-6,7,8,9-tetrahydropyrido[1,2-a]indol-10-yl}acetic acid

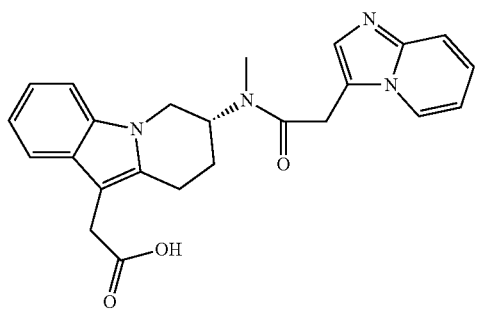 [SMILES: CN(C(=O)Cc1cnc2ccccn12)[C@@H]1CCc2c(CC(=O)O)c3ccccc3n2C1]

The title compound was prepared using analogous procedures described in Example 1 (Method A) from imidazo[1,2-a]pyridin-3-ylacetic acid and propyl [(7R)-7-(methylamino)-6,7,8,9-tetrahydropyrido[1,2-a]indol-10-yl]acetate. MS (+ESI) m/z: 417.

EXAMPLE 52

[(7S)-7-{[(4-fluorophenyl)acetyl](methyl)amino}-6,7,8,9-tetrahydropyrido[1,2-a]indol-10-yl]acetic acid

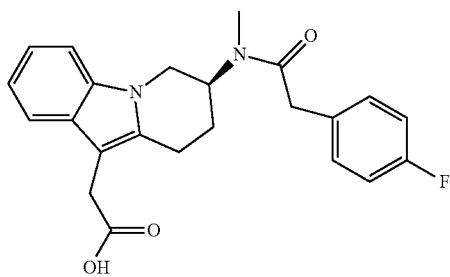 [SMILES: CN(C(=O)Cc1ccc(F)cc1)[C@H]1CCc2c(CC(=O)O)c3ccccc3n2C1]

Step 1: methyl [7-{[(4-fluorophenyl)sulfonyl](methyl)amino}-6,7,8,9-tetrahydropyrido[1,2-a]indol-10-yl]acetate
This compound may be prepared according to the general procedures outlined in WO2007019675.
Step 2: methyl [(7S)-7-{[(4-fluorophenyl)sulfonyl](methyl)amino}-6,7,8,9-tetrahydropyrido[1,2-a]indol-10-yl]acetate
The methyl [7-{[(4-fluorophenyl)sulfonyl](methyl)amino]-6,7,8,9-tetrahydropyrido[1,2-a]indol-10-yl}acetate was resolved by chiral HPLC using a ChiralpakAD column and eluting with a mixture of 20% EtOH/20% iPrOH/60% Hex to afford equal amounts of methyl [(7S)-7-{[(4-fluorophenyl)sulfonyl](methyl)amino}-6,7,8,9-tetrahydropyrido[1,2-a]indol-10-yl]acetate (retention time=5.90 min (>99% ee)) and methyl [(7R)-7-{[(4-fluorophenyl)sulfonyl](methyl)amino}-6,7,8,9-tetrahydropyrido[1,2-a]indol-10-yl]acetate (retention time=13.31 min (>99% ee))
Step 3: methyl [(7S)-7-(methylamino)-6,7,8,9-tetrahydropyrido[1,2-a]indol-10-yl]acetate
The deprotection of the amine was achieved according to the general procedures outlined in Scheme 111 (See Monika Fitz Tetrahedron Asymmetry 2005, 16, 3690 for examples of sulfonamide cleavage).
Step 4: [(7S)-7-{[(4-fluorophenyl)acetyl](methyl)amino}-6,7,8,9-tetrahydropyrido[1,2-a]indol-10-yl]acetic acid
The title compound was prepared using analogous procedures described in Example 1 (Method A) from (4-fluorophenyl)acetic acid and methyl [(7S)-7-(methylamino)-6,7,8,9-tetrahydropyrido[1,2-a]indol-10-yl]acetate. MS (+ESI) m/z: 395.

EXAMPLE 53

((7R)-7-{[4-(4-Fluoro-phenyl)-tetrahydro-pyran-4-carbonyl]-methyl-amino}-6,7,8,9-tetrahydropyrido[1,2-a]indol-10-yl)-acetic acid

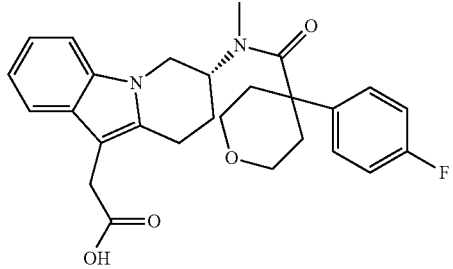 [SMILES: CN(C(=O)C1(c2ccc(F)cc2)CCOCC1)[C@@H]1CCc2c(CC(=O)O)c3ccccc3n2C1]

The title compound was prepared using analogous procedures described in Example 1 (Method A) from 4-(4-fluorophenyl)tetrahydro-2H-pyran-4-carboxylic acid and propyl [(7R)-7-(methylamino)-6,7,8,9-tetrahydropyrido[1,2-a]indol-10-yl]acetate. MS (+ESI) m/z: 465.

EXAMPLE 54

{(7R)-7-[(2-Methoxy-2-phenyl-acetyl)-methyl-amino]-6,7,8,9-tetrahydro-pyrido[1,2-a]indol-10-yl}-acetic acid

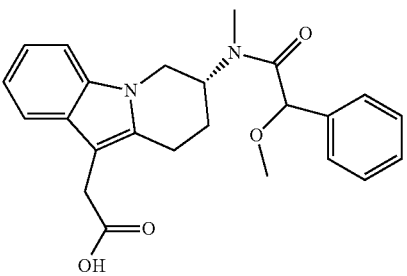 [SMILES: COC(C(=O)N(C)[C@@H]1CCc2c(CC(=O)O)c3ccccc3n2C1)c1ccccc1]

The title compound was prepared using analogous procedures described in Example 1 (Method A) from methoxy (phenyl)acetic acid and propyl [(7R)-7-(methylamino)-6,7,8,9-tetrahydropyrido[1,2-a]indol-10-yl]acetate. MS (+ESI) m/z: 407.

EXAMPLE 55

[(7R)-7-{methyl[(2R or 2S)-2-phenylpropanoyl]amino}-6,7,8,9-tetrahydropyrido[1,2-a]indol-10-yl]acetic acid

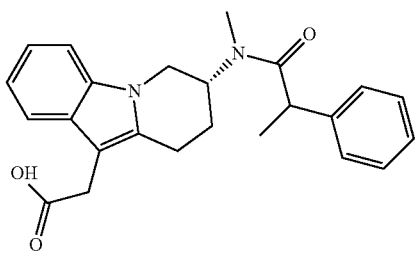 [SMILES: CC(C(=O)N(C)[C@@H]1CCc2c(CC(=O)O)c3ccccc3n2C1)c1ccccc1]

The title compound was prepared using analogous procedures described in Example 1 (Method A) from 2-phenylpropanoic acid and propyl [(7R)-7-(methylamino)-6,7,8,9-tetrahydropyrido[1,2-a]indol-10-yl]acetate. The separation of the resulting diastereoisomers was performed at the ester stage on chiral HPLC using a 4.6×250 mm Chiralcel OD column eluting with 30% iPrOH, 69.75% Hexanes and 0.25% HCOOH at 1 mL/min and 254 nm. Retention times=5.0 and 8.1 min. The two resulting esters were hydrolyzed separately to afford EXAMPLE 55.1 and 55.2 respectively. MS (+ESI) m/z: 391.

EXAMPLE 56

{(7R)-7-[Methyl-(1,2,3,4-tetrahydro-naphthalene-1-carbonyl)-amino]-6,7,8,9-tetrahydropyrido[1,2-a]indol-10-yl}-acetic acid

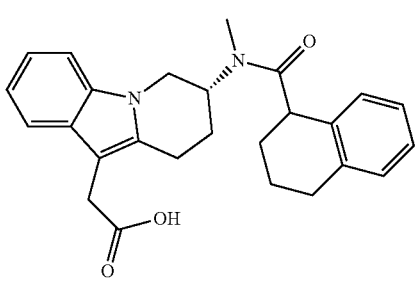 [SMILES: CN(C(=O)C1CCCc2ccccc21)[C@@H]1CCc2c(CC(=O)O)c3ccccc3n2C1]

The title compound was prepared using analogous procedures described in Example 1 (Method A) from 1,2,3,4-tetrahydronaphthalene-1-carboxylic acid and propyl [(7R)-7-(methylamino)-6,7,8,9-tetrahydropyrido[1,2-a]indol-10-yl]acetate. MS (+ESI) m/z: 417.

EXAMPLE 57

((7R)-7-{[2-(4-Dimethylamino-phenyl)-acetyl]-methyl-amino}-6,7,8,9-tetrahydro-pyrido[1,2-a]indol-10-yl)-acetic acid

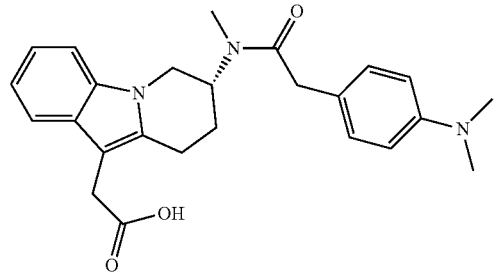 [SMILES: CN(C)c1ccc(CC(=O)N(C)[C@@H]2CCc3c(CC(=O)O)c4ccccc4n3C2)cc1]

The title compound was prepared using analogous procedures described in Example 1 (Method A) from [4-(dimethylamino)phenyl]acetic acid and propyl [(7R)-7-(methylamino)-6,7,8,9-tetrahydropyrido[1,2-a]indol-10-yl]acetate. MS (+ESI) m/z: 420.

EXAMPLE 58

{(7R)-7-[(2-Cyclopentyl-acetyl)-methyl-amino]-6,7,8,9-tetrahydro-pyrido[1,2-a]indol-10-yl}-acetic acid

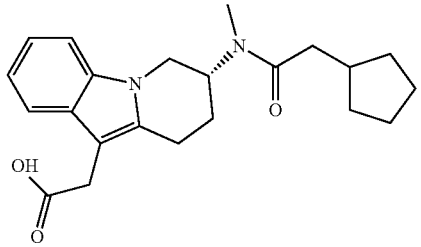 [SMILES: CN(C(=O)CC1CCCC1)[C@@H]1CCc2c(CC(=O)O)c3ccccc3n2C1]

The title compound was prepared using analogous procedures described in Example 1 (Method A) from cyclopentylacetic acid and propyl [(7R)-7-(methylamino)-6,7,8,9-tetrahydropyrido[1,2-a]indol-10-yl]acetate. MS (+ESI) m/z: 369.

EXAMPLE 59

((7R)-7-{Methyl-[3-(piperidine-1-sulfonyl)-benzoyl]-amino}-6,7,8,9-tetrahydro-pyrido[1,2-a]indol-10-yl)-acetic acid

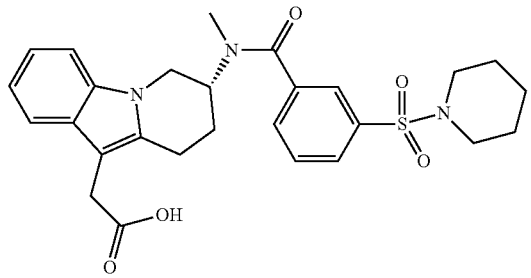 [SMILES: CN(C(=O)c1cccc(S(=O)(=O)N2CCCCC2)c1)[C@@H]1CCc2c(CC(=O)O)c3ccccc3n2C1]

The title compound was prepared using analogous procedures described in Example 1 (Method A) from 3-(piperidin- 1-ylsulfonyl)benzoic acid and propyl [(7R)-7-(methylamino)-6,7,8,9-tetrahydropyrido[1,2-a]indol-10-yl]acetate. MS (+ESI) m/z: 510.

EXAMPLE 60

{(7R)-7-[Methyl-(2-pyridin-2-yl-propionyl)-amino]-6,7,8,9-tetrahydro-pyrido[1,2-a]indol-10-yl}-acetic acid

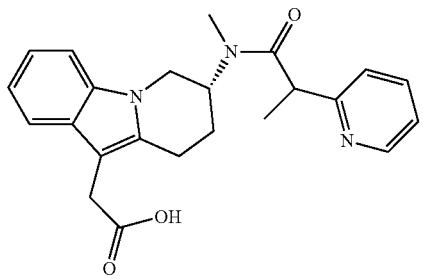 [SMILES: CC(C(=O)N(C)[C@@H]1CCc2c(CC(=O)O)c3ccccc3n2C1)c1ccccn1]

The title compound was prepared using analogous procedures described in Example 1 (Method A) from 2-(pyridin-2-yl)propanoic acid and propyl [(7R)-7-(methylamino)-6,7,8,9-tetrahydropyrido[1,2-a]indol-10-yl]acetate. MS (+ESI) m/z: 392.

EXAMPLE 61

((7R)-4-Fluoro-7-{[(2R or 2S)-2-(4-fluoro-phenyl)-propionyl]-methyl-amino}-6,7,8,9-tetrahydropyrido[1,2-a]indol-10-yl)-acetic acid

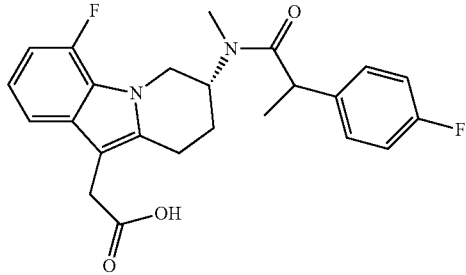 [SMILES: CC(C(=O)N(C)[C@@H]1CCc2c(CC(=O)O)c3cccc(F)c3n2C1)c1ccc(F)cc1]

Step 1: 7-fluoroindole

This compound was prepared from 2-fluoro-phenylhydrazine according to the procedure outlined for propyl ([7R]-7-amino-6,7,8,9-tetrahydropyrido[1,2-a]indol-10-yl)acetate.

Step 2: propyl [(7R)-4-fluoro-7-(methylamino)-6,7,8,9-tetrahydropyrido [1,2-a]indol-10-yl]acetate This compound was prepared from 7-fluoroindole according to the general procedures outlined in Example 1 (step 1 and 2).

Step 3: ((7R)-4-Fluoro-7-{[2R or 2S)-2-(4-fluoro-phenyl)-propionyl]-methyl-amino}-6,7,8,9-tetrahydro-pyrido[1,2-a]indol-10-yl)-acetic acid The title compound was prepared using analogous procedures described in Example 1 (Method A) from 2-phenylpropanoic acid and propyl [(7R)-4-fluoro-7-(methylamino)-6,7,8,9-tetrahydropyrido[1,2-a]indol-10-yl]acetate. The chiral separation of the resulting diastereoisomers was performed on chiral HPLC using a 4.6×250 mm Chiralcel OD column eluting with 10% iPrOH, 89.75% Hexanes and 0.25% Et$_3$N at 1 mL/min and 254 nm. Retention times=9.7 and 13.4 min. The two resulting esters were hydrolyzed separately to afford EXAMPLE 61.1 and 61.2 respectively. MS (+ESI) m/z: 449.

Biological Assays

Radioligand binding assay. Radioligand binding assays were performed at room temperature in 10 mM HEPES/KOH pH 7.4, 1 mM EDTA containing 10 mM MnCl$_2$ and 0.7 nM [$^3$H]PGD$_2$ (NEN, 171 Ci mmol$^{-1}$), in a final volume of 0.2 ml. Competing ligands were diluted in dimethylsulfoxide (Me$_2$SO) that was kept constant at 1% (v/v) of the final incubation volume. The reaction was initiated by the addition of 8-20 μg of membrane protein prepared from a HEK-hCRTH2 cell line. Total and non-specific binding were determined in the absence and the presence of 10 μM PGD$_2$, respectively. Under these conditions, specific binding (total minus non-specific) of the radioligand to the receptor reached equilibrium within 50 min and was stable up to 180 min. The reaction was routinely conducted for 60 min at room temperature and terminated by rapid filtration through prewetted Unifilters GF/C (Packard), using a Tomtec MachIII semi-automated harvester (for HEK-hCRTH2). The filters were then washed with 4 ml of the same buffer and residual radioligand bound to the filter was determined by liquid scintillation counting following equilibration in 25 μl Ultima Gold F™ (Unifilter) (Packard). The Ki (in nM) values for representative compounds of the present invention are as follows: ≤5: Examples 1, 3, 5, 6, 20, 30, 31, 32, 35; >5 and ≤10: Examples, 2, 26, 29; >10 and ≤50: Examples 9, 19, 21, 23, 25, 36; >50 and ≤100: Examples 7, 34.

i[cAMP] measurements. HEK-hCRTH2 cells were grown to 80-90% confluency. On the day of the assay, the cells were washed with PBS, incubated for 2 min in cell dissociation buffer, harvested by centrifugation at 300 g for 5 mM at room temperature and resuspended at 1.25e10$^6$ cells ml$^{-1}$ in Hanks' balanced salt solution containing 20 mM HEPES pH 7.4 and 0.75 mM IBMX (HBSS/HEPES/IBMX). The assay was performed in 384-plate format with 0.01 ml HBSS/HEPES/IBMX per well containing 12 500 cells and 75 nl of the test compound at various concentrations. Following a 10 min pre-incubation of the cells with the test compound at 37° C., 0.005 ml of Forskolin/DK-PGD$_2$ dilute in HBSS 20 mM Hepes, was added at a respectively final concentration of 10 uM and 150 nM, to initiate the reaction. After 10 min incubation at 37° C., the cAMP content was quantified using the cAMP XS+ HitHunter chemiluminescence assay. (GE Healthcare 90-0075). % inhibition was calculated using the Forskolin and EC85 DK-PGD2 controls.

Eosinophil shape change assay in human whole blood. Blood was collected in vacutainers containing EDTA. The antagonist was added to blood and incubated for 10 min at room temperature. DK-PGD$_2$ (13,14-dihydro-15-keto prostaglandin D$_2$) was then added to blood for 4 min at 37° C. in a running water bath. Blood cells were then fixed in presence of cold 0.25% (v/v) paraformaldehyde prepared in 75% (v/v) PBS for 1 min on ice. 175 μL of fixed blood was transferred into 870 μL of cold 155 mM NH$_4$Cl lysis solution and incubated at 4° C. for at least 40 min. The solution was then centrifuged at 430 g for 5 min and the supernatant was discarded. Centrifuged cells were analyzed with a FACs Calibur flow cytometer (Becton Dickinson). Flow neutrophils based on their high autofluorescence and determining the percent of total eosinophils with increased FSC-H value. Maximum (100%) and minimum (0%) shape change were determined in the presence of 10 μM DK-PGD$_2$ and PBS, respectively. A dose response curve with DK-PGD$_2$ was performed with every assay to determine the EC$_{50}$ for each blood donor. Compounds were tested in 10-dose titration curves in the presence of 30 nM DK-PGD2 to determine an antagonist IC$_{50}$.

Some compounds of the present invention are selective for the CRTH2 receptor over the DP receptor. Assays on the DP, as well as other prostanoid, receptors are described in WO2003/06220.

What is claimed is:

1. A compound of the formula Ib:

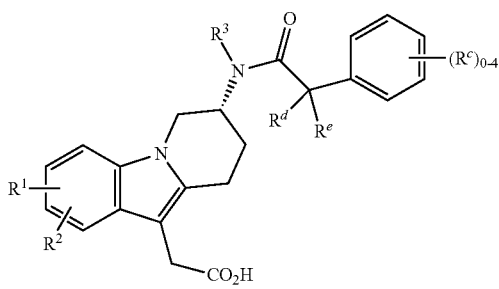

Ib and pharmaceutically acceptable salts thereof, wherein:
Y is methylene;
$R^1$ is selected from H, halogen, —$OC_{1-6}$alkyl, and —$C_{1-6}$alkyl;
$R^2$ is selected from H, halogen, —$C_{1-6}$alkyl, —$OC_{1-6}$alkyl, —$SC_{1-6}$alkyl, —$S(O)C_{1-6}$alkyl, —$S(O)_2C_{1-6}$alkyl, —CN, aryl and heteroaryl;
$R^3$ is selected from H, $C_{1-6}$alkyl and benzyl optionally substituted on the phenyl portion with 1 to 3 halogen;
$R^c$ is selected from halogen, $NR^fR^g$, $SO_2NR^fR^g$, CN, $C_{1-6}$alkoxy, $C_{1-6}$alkyl, halo$C_{1-6}$alkoxy, and halo$C_{1-6}$alkyl;
$R^d$ and $R^e$ are independently selected from hydrogen, $C_{1-6}$alkyl, —$C_{1-6}$alkyl-$C_{3-6}$cycloalkyl, hydroxy, $C_{1-6}$alkoxy, aryl optionally substituted with 1 to 3 groups independently selected from $R^c$, and $NR^fR^g$; or
$R^d, R^e$ together with the carbon atom to which they are both attached form a $C_{3-6}$cycloalkyl optionally having a ring heteroatom selected from —O—, —S—, —N(C(O)$R^f$)— and —N($R^f$)—, and optionally substituted with 1 to 3 $C_{1-3}$alkyl groups;
$R^f$ and $R^g$ are independently selected from hydrogen and $C_{1-3}$alkyl; or
$R^f, R^g$ together with the atom to which they are both attached form a 3- to 6-membered ring.

2. The compound of claim 1 wherein $R^d, R^e$ and the carbon to which they are both attached together form a $C_{3-6}$cycloalkyl optionally substituted with one or two $C_{1-3}$alkyl groups.

3. The compound of claim 1 selected from the group consisting of:
{(7R)-7-[[2-(4-fluorophenyl)propanoyl](methyl)amino]-6,7,8,9-tetrahydropyrido[1,2-a]indol-10-yl}acetic acid;
{(7R)-7-[[(4-fluorophenyl)acetyl](methyl)amino]-6,7,8,9-tetrahydropyrido[1,2-a]indol-10-yl}acetic acid;
((7R)-7-{(4-fluorobenzyl)[(4-fluorophenyl)acetyl]amino}-6,7,8,9-tetrahydropyrido[1,2-a]indol-10-yl)acetic acid;
[(7R)-7-({[1-(4-fluorophenyl)cyclopentyl]carbonyl}amino)-6,7,8,9-tetrahydropyrido[1,2-a]indol-10-yl]acetic acid;
{(7R)-7-[{[1-(4-fluorophenyl)cyclopentyl]carbonyl}(methyl)amino]-6,7,8,9-tetrahydropyrido[1,2-a]indol-10-yl}acetic acid;
{(7R)-7-[[2-(4-fluorophenyl)-2-methylpropanoyl](methyl)amino]-6,7,8,9-tetrahydropyrido[1,2-a]indol-10-yl}acetic acid;
{(7R)-7-[[(2,4-difluorophenyl)acetyl](methyl)amino]-6,7,8,9-tetrahydropyrido[1,2-a]indol-10-yl}acetic acid;
{(7R)-7-[[(2-chloro-4-fluorophenyl)acetyl](methyl)amino]-6,7,8,9-tetrahydropyrido[1,2-a]indol-10-yl}acetic acid;
{(7R)-7-[[(3-chloro-4-fluorophenyl)acetyl](methyl)amino]-6,7,8,9-tetrahydropyrido[1,2-a]indol-10-yl}acetic acid;
{(7R)-7-[{[4-fluoro-2-(trifluoromethyl)phenyl]acetyl}(methyl)amino]-6,7,8,9-tetrahydropyrido[1,2-a]indol-10-yl}acetic acid;
{(7R)-7-[{[4-fluoro-3-(trifluoromethyl)phenyl]acetyl}(methyl)amino]-6,7,8,9-tetrahydropyrido[1,2-a]indol-10-yl}acetic acid;
{(7R)-7-[[(2-(2-bromo-4-fluorophenyl)propanoyl](methyl)amino]-6,7,8,9-tetrahydropyrido[1,2-a]indol-10-yl}acetic acid;
(7R)-7-[[(4-chlorophenyl)acetyl](methyl)amino]-6,7,8,9-tetrahydropyrido[1,2-a]indol-10-yl}acetic acid;
{(7R)-7-[{[1-(4-chlorophenyl)cyclopentyl]carbonyl}(methyl)amino]-6,7,8,9-tetrahydropyrido[1,2-a]indol-10-yl}acetic acid;
{(7R)-7-[[(4-methoxyphenyl)acetyl](methyl)amino]-6,7,8,9-tetrahydropyrido[1,2-a]indol-10-yl}acetic acid;
{(7R)-7-[methyl(phenylacetyl)amino]-6,7,8,9-tetrahydropyrido[1,2-a]indol-10-yl}acetic acid;
{(7R)-7-[[(3,4-difluorophenyl)acetyl](methyl)amino]-6,7,8,9-tetrahydropyrido[1,2-a]indol-10-yl}acetic acid;
[(7R)-7-(methyl{[4-(trifluoromethyl)phenyl]acetyl}amino)-6,7,8,9-tetrahydropyrido[1,2-a]indol-10-yl]acetic acid;
((7R)-7-{methyl[2-phenylpropanoyl]amino}-6,7,8,9-tetrahydropyrido[1,2-c]indol1-10-yl)-acetic acid;
{(7R)-7-[{[1-(4-fluorophenyl)cyclopropyl]carbonyl}(methyl)amino]-6,7,8,9-tetrahydropyrido[1,2-a]indol-10-yl}acetic acid;
{(7R)-7-[{[1-(4-fluorophenyl)cyclobutyl]carbonyl}(methyl)amino]-6,7,8,9-tetrahydropyrido[1,2-a]indol-10-yl}acetic acid;
{(7R)-7-[[2-(4-fluorophenyl)-2-piperidin-1-ylacetyl](methyl)amino]-6,7,8,9-tetrahydropyrido[1,2-a]indol-10-yl}acetic acid;
{(7R)-7-[[(2-bromo-4-fluorophenyl)acetyl](methyl)amino]-6,7,8,9-tetrahydropyrido[1,2-a]indol-10-yl}acetic acid;
{(7R)-7-[{[1-(4-fluorophenyl)-2,2-dimethylcyclopropyl]carbonyl}(methyl)amino]-6,7,8,9-tetrahydropyrido[1,2-a]indol-10-yl}acetic acid;
{(7R)-7-[[-2-methoxy-2-phenylacetyl](methyl)amino]-6,7,8,9-tetrahydropyrido[1,2-a]indol-10-yl}acetic acid;
((7R)-7-{[2,2-bis-(4-fluoro-phenyl)-acetyl]-methyl-amino}-6,7,8,9-tetrahydro-pyrido[1,2-a]indol-10-yl)-acetic acid;
{(7R)-7-[(diphenylacetyl)(methyl)amino]-6,7,8,9-tetrahydropyrido[1,2-a]indol-10-yl}acetic acid;
{(7R)-7-[(diphenylacetyl)(methyl)amino]-6,7,8,9-tetrahydropyrido[1,2-a]indol-10-yl}acetic acid;
((7R)-7-{[3-cyclopropyl-2-(4-fluoro-phenyl)-propionyl]-methyl-amino}-6,7,8,9-tetrahydro-pyrido[1,2-a]indol-10-yl)-acetic acid;
[(7R)-7-{[(2R)-2-hydroxy-2-phenylpropanoyl](methyl)amino}-6,7,8,9-tetrahydropyrido[1,2-a]indol-10-yl] acetic acid;
[(7R)-7-{[(2S)-2-hydroxy-2-phenylpropanoyl](methyl)amino}-6,7,8,9-tetrahydropyrido[1,2-a]indol-10-yl] acetic acid;

((7R)-7-{ethyl-[1-(4-fluoro-phenyl)-cyclopropanecarbonyl]-amino}-6,7,8,9-tetrahydropyrido[1,2-a]indol-10-yl)-acetic acid ((7R)-7-{[4-(4-fluoro-phenyl)-tetrahydro-pyran-4-carbonyl]-methyl-amino}-6,7,8,9-tetrahydro-pyrido[1,2-a]indol-10-yl)-acetic acid;

{(7R)-7-[(2-methoxy-2-phenyl-acetyl)-methyl-amino]-6,7,8,9-tetrahydro-pyrido[1,2-a]indol-10-yl}-acetic acid;

[(7R)-7-{methyl[(2R or 2S)-2-phenylpropanoyl]amino}-6,7,8,9-tetrahydropyrido[1,2-a]indol-10-yl]acetic acid;

((7R)-7-{[2-(4-dimethylamino-phenyl)-acetyl]-methyl-amino}-6,7,8,9-tetrahydropyrido[1,2-a]indol-10-yl)-acetic acid; and ((7R)-4-fluoro-7-{[(2R or 2S)-2-(4-fluorophenyl)-propionyl]-methyl-amino}-6,7,8,9-tetrahydro-pyrido[1,2-a]indol-10-yl)-acetic acid, or a pharmaceutically acceptable salt thereof.

4. The compound of claim 1 selected from the group consisting of:

{(7R)-7-[[2-(4-fluorophenyl)propanoyl](methyl)amino]-6,7,8,9-tetrahydropyrido[1,2-a]-indol-10-yl}acetic acid;

((7R)-7-{(4-fluorobenzyl)[(4-fluorophenyl)acetyl]amino}-6,7,8,9-tetrahydropyrido[1,2-a]-indol-10-yl)acetic acid;

{(7R)-7-[{[1-(4-fluorophenyl)cyclopentyl]carbonyl}(methyl)amino]-6,7,8,9-tetrahydropyrido[1,2-a]indol-10-yl}acetic acid;

{(7R)-7-[[2-(4-fluorophenyl)-2-methylpropanoyl](methyl)amino]-6,7,8,9-tetrahydropyrido[1,2-a]indol-10-yl}acetic acid;

{(7R)-7-[{[1-(4-chlorophenyl)cyclopentyl]carbonyl}(methyl)amino]-6,7,8,9-tetrahydropyrido[1,2-a]indol-10-yl}acetic acid;

((7R)-7-{methyl[2-phenylpropanoyl]amino}-6,7,8,9-tetrahydropyrido[1,2-a]indol-10-yl)-acetic acid;

{(7R)-7-[{[1-(4-fluorophenyl)cyclopropyl]carbonyl}(methyl)amino]-6,7,8,9-tetrahydropyrido[1,2-a]indol-10-yl}acetic acid;

{(7R)-7-[{[1-(4-fluorophenyl)cyclobutyl]carbonyl}(methyl)amino]-6,7,8,9-tetrahydropyrido[1,2-a]indol-10-yl}acetic acid; and {(7R)-7-[{[1-(4-fluorophenyl)-2,2-dimethylcyclopropyl]carbonyl}(methyl)amino]-6,7,8,9-tetrahydropyrido[1,2-a]indol-10-yl}acetic acid, or a pharmaceutically acceptable salt thereof.

5. A pharmaceutical composition comprising a therapeutically effective amount of the compound of claim 1 or a pharmaceutically acceptable salt thereof and a pharmaceutically acceptable carrier.

6. The compound of claim 1 or a pharmaceutically acceptable salt thereof, wherein the compound is {(7R)-7-[[2-(4-fluorophenyl)propanoyl](methyl)amino]-6,7,8,9-tetrahydropyrido[1,2-a]indol-10-yl}acetic acid.

7. The compound of claim 1 or a pharmaceutically acceptable salt thereof, wherein the compound is ((7R)-7-{(4-fluorobenzyl)[(4-fluorophenyl)acetyl]amino}-6,7,8,9-tetrahydropyrido[1,2-a]indol-10-yl)acetic acid.

8. The compound of claim 1 or a pharmaceutically acceptable salt thereof, wherein the compound is {(7R)-7-[{[1-(4-fluorophenyl)cyclopentyl]carbonyl}(methyl)amino]-6,7,8,9-tetrahydropyrido[1,2-a]indol-10-yl}acetic acid.

9. The compound of claim 1 or a pharmaceutically acceptable salt thereof, wherein the compound is {(7R)-7-[{[1-(4-fluorophenyl)-2,2-dimethylcyclopropyl]carbonyl}(methyl)amino]-6,7,8,9-tetrahydropyrido[1,2-a]indol-10-yl}acetic acid.

10. The compound of claim 1 or a pharmaceutically acceptable salt thereof, wherein the compound is ((7R)-4-fluoro-7-{[(2R or 2S)-2-(4-fluorophenyl)-propionyl]-methyl-amino}-6,7,8,9-tetrahydro-pyrido[1,2-a]indol-10-yl)-acetic acid.

* * * * *